(12) United States Patent
Pinkel et al.

(10) Patent No.: US 8,283,181 B2
(45) Date of Patent: Oct. 9, 2012

(54) CAPILLARY PINS FOR HIGH-EFFICIENCY MICROARRAY PRINTING DEVICE

(75) Inventors: Daniel Pinkel, Walnut Creek, CA (US);
Donna G. Albertson, Lafayette, CA (US); Greg Hamilton, San Francisco, CA (US); Nils W. Brown, San Francisco, CA (US); Robert Nordmeyer, San Leandro, CA (US)

(73) Assignee: The Regents of the University of California, Oakland, CA (US)

( * ) Notice: Subject to any disclaimer, the term of this patent is extended or adjusted under 35 U.S.C. 154(b) by 1036 days.

(21) Appl. No.: 12/169,863

(22) Filed: Jul. 9, 2008

(65) Prior Publication Data
US 2009/0029876 A1    Jan. 29, 2009

Related U.S. Application Data

(60) Division of application No. 11/017,625, filed on Dec. 15, 2004, now Pat. No. 7,402,286, which is a continuation-in-part of application No. 10/456,943, filed on Jun. 6, 2003, now Pat. No. 7,312,068, and a continuation-in-part of application No. PCT/US02/20766, filed on Jun. 27, 2002, said application No. 10/456,943 is a continuation-in-part of application No. 09/894,863, filed on Jun. 27, 2001, now Pat. No. 6,855,538, said application No. PCT/US02/20766 is a continuation-in-part of application No. 09/894,863.

(51) Int. Cl.
*G01N 1/10* (2006.01)

(52) U.S. Cl. ........... 436/180; 436/54; 436/807; 422/501

(58) Field of Classification Search .......... 422/501–504, 422/520–522; 73/863.32, 864, 864.01, 864.11, 73/864.13, 864.16, 864.24; 436/180, 54, 436/807
See application file for complete search history.

(56) References Cited

U.S. PATENT DOCUMENTS

| | | | |
|---|---|---|---|
| 3,641,823 A | 2/1972 | Harris et al. |
| 3,754,863 A | 8/1973 | Reunanen |
| 4,106,911 A | 8/1978 | Marcelli |
| 4,120,205 A | 10/1978 | Ripphahn et al. |
| 4,276,048 A | 6/1981 | Leaback |

(Continued)

FOREIGN PATENT DOCUMENTS

DE    2000 2314/00    11/2000

(Continued)

OTHER PUBLICATIONS

US Office Action dated Feb. 25, 2004 issued in U.S. Appl. No. 09/894,863.

(Continued)

*Primary Examiner* — Brian R Gordon
(74) *Attorney, Agent, or Firm* — Tom Hunter; Weaver Austin Villeneuve & Sampson LLP

(57) ABSTRACT

This invention provides improved components (e.g. array "pins", print head, substrate platen, print head platen, and the like) for microarray printing devices as well as microarray printing devices incorporating such components. In one embodiment, this invention provides a microarray print head comprising a plurality of glass or quartz spotting capillaries disposed in a support that maintains a fixed spacing between the spotting capillaries and that permits the spotting capillaries to move in a direction parallel to the long axis of the capillaries.

44 Claims, 18 Drawing Sheets

U.S. PATENT DOCUMENTS

| | | | |
|---|---|---|---|
| 4,498,510 A | | 2/1985 | Minshew, Jr. et al. |
| 4,613,238 A | | 9/1986 | Sachs |
| 4,830,832 A | * | 5/1989 | Arpagaus et al. ............... 422/65 |
| 4,981,783 A | | 1/1991 | Augenlicht |
| 5,073,343 A | | 12/1991 | Hukuhara et al. |
| 5,143,854 A | | 9/1992 | Pirrung et al. |
| 5,226,462 A | | 7/1993 | Carl |
| 5,384,261 A | | 1/1995 | Winkler et al. |
| 5,497,670 A | | 3/1996 | Carl |
| 5,525,464 A | | 6/1996 | Drmanac et al. |
| 5,525,515 A | | 6/1996 | Blattner |
| 5,700,637 A | | 12/1997 | Southern |
| 5,736,105 A | | 4/1998 | Astle |
| 5,744,305 A | | 4/1998 | Fodor et al. |
| 5,770,151 A | | 6/1998 | Roach et al. |
| 5,770,367 A | | 6/1998 | Southern et al. |
| 5,800,662 A | | 9/1998 | Bullen et al. |
| 5,807,522 A | | 9/1998 | Brown et al. |
| 5,849,598 A | | 12/1998 | Wilson et al. |
| 5,882,597 A | | 3/1999 | Astle |
| 5,958,343 A | | 9/1999 | Astle |
| 6,006,800 A | * | 12/1999 | Nakano .................. 141/130 |
| 6,040,138 A | | 3/2000 | Lockhart et al. |
| 6,083,763 A | | 7/2000 | Balch |
| 6,101,946 A | | 8/2000 | Martinsky |
| 6,110,426 A | | 8/2000 | Shalon et al. |
| 6,235,473 B1 | | 5/2001 | Friedman et al. |
| 6,258,324 B1 | | 7/2001 | Yiu |
| 6,308,750 B1 | | 10/2001 | Burke |
| 6,309,891 B1 | | 10/2001 | Shalon et al. |
| 6,323,043 B1 | | 11/2001 | Caren et al. |
| 6,325,114 B1 | * | 12/2001 | Bevirt et al. ............... 141/130 |
| 6,365,349 B1 | | 4/2002 | Moynihan et al. |
| 6,374,683 B1 | | 4/2002 | Hunicke-Smith et al. |
| 6,379,895 B1 | | 4/2002 | Fodor et al. |
| 6,391,625 B1 | | 5/2002 | Park et al. |
| 6,410,229 B1 | | 6/2002 | Lockhart et al. |
| 6,416,719 B1 | | 7/2002 | Fawcett et al. |
| 6,416,952 B1 | | 7/2002 | Pirrung et al. |
| 6,447,723 B1 | | 9/2002 | Schermer et al. |
| 6,506,611 B2 | * | 1/2003 | Bienert et al. ............... 436/180 |
| 6,521,187 B1 | | 2/2003 | Papen |
| 6,551,557 B1 | | 4/2003 | Rose et al. |
| 6,589,483 B1 | | 7/2003 | Maeda |
| 6,592,825 B2 | | 7/2003 | Pelc et al. |
| 6,824,024 B2 | | 11/2004 | Ingenhoven et al. |
| 6,855,538 B2 | | 2/2005 | Pinkel et al. |
| 6,866,825 B2 | | 3/2005 | Chiou et al. |
| 6,869,571 B2 | | 3/2005 | Ingenhoven et al. |
| 6,887,431 B1 | | 5/2005 | Vann et al. |
| 7,160,511 B2 | | 1/2007 | Takahashi et al. |
| 7,312,068 B2 | | 12/2007 | Pinkel et al. |
| 7,314,598 B2 | * | 1/2008 | Nishino .................. 422/501 |
| 7,402,286 B2 | | 7/2008 | Pinkel et al. |
| 2002/0110900 A1 | | 8/2002 | Jovanovich et al. |
| 2003/0003458 A1 | | 1/2003 | Pinkel et al. |
| 2003/0003596 A1 | | 1/2003 | Pawliszyn |
| 2003/0177849 A1 | | 9/2003 | Matsuda et al. |
| 2003/0190264 A1 | | 10/2003 | Yiu |
| 2004/0033554 A1 | | 2/2004 | Powers |
| 2004/0047765 A1 | | 3/2004 | Gordon et al. |
| 2004/0071603 A1 | | 4/2004 | Pinkel et al. |
| 2005/0163665 A1 | | 7/2005 | Gumbrecht et al. |
| 2005/0169808 A1 | | 8/2005 | Pinkel et al. |
| 2005/0181519 A1 | | 8/2005 | Karg et al. |
| 2005/0235762 A1 | | 10/2005 | Sinclair |
| 2006/0144169 A1 | * | 7/2006 | Porat et al. .................. 73/864.14 |
| 2007/0025880 A1 | | 2/2007 | Hoummady |
| 2007/0092410 A1 | * | 4/2007 | Ricker et al. .................. 422/100 |

FOREIGN PATENT DOCUMENTS

| | | |
|---|---|---|
| EP | 1 101 616 | 5/2001 |
| WO | WO 95/25116 | 9/1995 |
| WO | WO 01/71035 | 9/2001 |
| WO | WO 03/003277 | 1/2003 |

OTHER PUBLICATIONS

US Notice of Allowance dated Oct. 1, 2004 issued in U.S. Appl. No. 09/894,863.

US Office Action dated Sep. 23, 2005 issued in U.S. Appl. No. 10/456,943.

US Office Action Final dated Aug. 15, 2006 issued in U.S. Appl. No. 10/456,943.

US Notice of Allowance dated Aug. 9, 2007 issued in U.S. Appl. No. 10/456,943.

US Office Action dated Jun. 21, 2007 issued in U.S. Appl. No. 11/017,625.

US Notice of Allowance dated Mar. 17, 2008 issued in U.S. Appl. No. 11/017,625.

PCT International Search Report dated Jan. 14, 2003 issued in PCT/US02/20766 (WO 03/003277 A3).

* cited by examiner

CAPILLARY PINS FOR HIGH-EFFICIENCY MICROARRAY PRINTING DEVICE

CROSS-REFERENCE TO RELATED APPLICATIONS

This application is a divisional of U.S. Ser. No. 11/017,625, filed Dec. 15, 2004, now U.S. Pat. No. 7,402,286, which is a continuation-in-part of U.S. Ser. No. 10/456,943, filed Jun. 6, 2003, now U.S. Pat. No. 7,312,068, and PCT/US02/20766, filed Jun. 27, 2002 both of which are continuations-in-part of U.S. Ser. No. 09/894,863, filed on Jun. 27, 2001, now U.S. Pat. No. 6,855,538, all of which are incorporated herein by reference in their entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to the field of high-density microarray production. In particular, this invention provides methods and devices that permit high-density arrays to be printed with significantly smaller feature size and spacing and greatly improved reagent usage.

BACKGROUND OF THE INVENTION

The immobilization of test molecules or "probes" on array supports has had a significant impact on drug discovery, medical diagnostic methods, and basic research. The use of high-density microarrays of organic molecules permits literally thousands of assays to be simultaneously performed on one or more samples. Using high-density microarrays, numerous analytes can be simultaneously detected and/or quantified permitting the rapid characterization of complex systems (e.g. complex assays for gene expression). High-density microarrays are also useful for "high-throughput" screening assays, diagnostics, and in many other contexts. The ability to manufacture microarrays in an efficient and cost-effective manner is of considerable interest to researchers worldwide and of significant commercial value.

In general, microarrays of greater density are preferred. A higher density array typically allows more assays to be performed simultaneously and/or, for lower sample volumes to be used for the same number of assays. In providing large, high-density arrays of molecules (e.g., probes or analytes) there are a number of considerations. The array elements (e.g. dots) should be substantially reproducible in size, particularly if one wishes to quantify an analyte. In addition, the array elements should be consistently and reliably positioned, and should be highly reproducible.

The basic approaches for generating arrays of test molecules such as nucleic acid, protein or other organic molecules fall into two general categories. In the first such approach the test molecules are directly synthesized onto the array support, while in the second such approach the test molecules are attached to the support post-synthetically. Each approach has its own limitations and drawbacks. For example, when an array is created by direct synthesis onto an array support, the efficiency of each synthetic step affects the quality and integrity of molecules forming the array. The magnitude of the problem increases with the complexity of the individual molecules, potentially resulting in an undesirable percentage of incorrectly synthesized molecules and incomplete sequences. Such contaminants can interfere with subsequent use of the array.

In addition, synthetic approaches (e.g. as described by Southern et al. (U.S. Pat. Nos. 5,770,367, 5,700,637, and 5,436,327), Pirrung et al. (U.S. Pat. No. 5,143,854), Fodor et al. (U.S. Pat. Nos. 5,744,305 and 5,800,992), and Winkler et al. (U.S. Pat. No. 5,384,261), are generally unable to construct microarrays of large macromolecules. Such technologies can also be expensive and difficult to implement.

In contrast, the second approach to array production allows the desired molecules to be produced (e.g. synthesized, isolated, amplified, e.g.) by conventional methods prior to their formation into an array. Consequently, the quality of the arrayed molecules, and thus the quality of the resultant array, is potentially greater than that produced by the direct synthesis approach.

Such "spotting" approaches include, but are not limited to inkjet, and direct surface contact printing. Inkjet devices require high reagent volumes and risk "probe" degradation during volatilization.

Direct surface contact printing (see, e.g., U.S. Pat. Nos. 4,981,783, 5,525,464, 5,770,151, and 5,807,522), are limited in their ability to reliably, reproducibly, and uniformly apply the array elements to the array substrate. Reagent usage is also relatively inefficient, and array density is limited.

SUMMARY OF THE INVENTION

The present invention provides improved components (e.g. array "pins", print head, substrate platen, print head platen, and the like) for microarray printing devices as well as microarray printing devices incorporating such components. In particular, methods and devices of this invention permit high-density arrays to be printed with significantly smaller feature size and spacing, and greatly improved reagent usage.

In one embodiment this invention provides a microarray print head, said print head comprising a plurality of glass or quartz (or other mineral), or ceramic, or porcelain, or ceramic spotting capillaries disposed in a support that maintains a fixed spacing between the spotting capillaries and that permits the spotting capillaries to move in a direction parallel to the long axis of the capillaries (i.e. the spotting capillaries can slide through the support). Preferred spotting capillaries are microcapillary tubes and particularly preferred spotting capillaries have a tapered tip (e.g. a ground, beveled tip). The capillaries can have any desirable cross-section (e.g. round, ovoid, square, triangular, irregular), however preferred capillaries are round in cross-section.

In certain preferred embodiments, the capillaries have a maximum load volume of about 0.5 mL. In certain preferred embodiments, the spotting capillaries have a load volume of about 0.2 mL.

Preferred print heads comprise at least 4 spotting capillaries, preferably least, 4, 16, 32, 64, or 128 spotting capillaries and in certain preferred embodiments, the spacing between two adjacent spotting capillaries is about 3 mm or less, center to center.

In certain preferred embodiments, the spotting capillaries have detents where the spotting capillaries have a rest position in which the detents contact a support stopping the movement of the spotting capillaries in a direction toward the substrate that is to be printed. The print head can also comprise a spring attached to a spotting capillary where, in the absence of a force against the printing tip of the spotting capillary the spring returns said spotting capillary to a rest position. The print head can be provided separately or can be found as a component in a microarray printing device.

In preferred embodiments, the spotting capillaries are in fluid communication (e.g. via flexible capillary tubing) with a manifold. In preferred embodiments, the manifold comprises a common port and a plurality of individual ports where an aperture into an individual port is disposed inward of the inside wall of the manifold. The manifold can be connected to a gas and/or vacuum source.

In another embodiment, this invention provides a microarray print head, the print head comprising a plurality of spotting capillaries disposed in a support that permits the spotting capillaries to move in a direction parallel to the long axis of the capillaries, where the capillaries are coupled to; a vacuum chamber through which the capillaries and the pistons are disposed; a port in the vacuum chamber to which a vacuum can be applied; where the pistons and capillaries are disposed such that increasing the vacuum in the chamber increases the force holding the pistons into the chamber and thereby increases the resistance of the capillaries to deflection away from a printing substrate. In various embodiments the each capillary can be coupled to a single piston or one or more capillaries (e.g., 2, 5, 10, 20, 50, 100, all, etc.) are coupled to a single piston. In certain embodiments the print head further comprises a means (e.g., a vacuum valve, and/or a valve to atmosphere, and/or a variable vacuum source, etc.) for adjusting the vacuum in the vacuum chamber. In various embodiments the lower wall of the vacuum chamber comprises a plurality of tapered guide holes in which the capillaries are disposed. In certain embodiments the lower wall of the chamber comprises two or more guide plates such that lateral movement of the capillaries is constrained at two or more positions or In various embodiments two guide plates such that lateral movement of the capillaries is constrained at only two positions. In various embodiments the spotting capillaries pass through the upper end of the pistons. In various embodiments the spotting capillaries are attached to the upper portion of the pistons at the upper portion of the capillaries. Typically the spacing of the capillaries accommodates a standard (e.g., 96, 384, 864, 1536 well, etc.) microtiter plate. In certain embodiments where the spacing between two adjacent spotting capillaries is about 3 mm or less, center to center. In various embodiments the spotting capillaries are glass or quartz and can preferably comprise a beveled (e.g., ground) tip. In certain embodiments a capillary comprising the print head has maximum load volume of about 0.5 µL, 0.05 µl, 0.2 µl, etc. In certain embodiments the print head comprises at least 4, preferably at least 8, more preferably at least 16, 32, 64, 128, 192, or 256 spotting capillaries. In certain embodiments the print head comprises from 16 to about 256 capillaries. In various embodiments the print heads described herein are in a microarray printing device. In various embodiments the capillaries are in fluid communication with a manifold. In certain embodiments the manifold comprises at least one common port and individual ports where an aperture into an individual port is disposed inward of the inside wall of the manifold.

In certain embodiments this invention provides a microarray printing device, comprising a microarray print head as described herein and a microarray substrate holder attached to a platen. In certain embodiments the microarray substrate holder comprises one or more vacuum ports under the substrate when the substrate is place on the platen. Various substrate holders can optionally comprise locating pins to position each substrate. In certain embodiments the microarray substrate holder comprises a spring loaded retainer. In certain embodiments the printing device can print at least about 1500 to about 2000 array elements per spotting capillary per load. In certain embodiments the printing device can print array elements with a precision of at least 30 µm, preferably at least about 10 µm, more preferably at least about 5 µm precision. In certain embodiments the printing device can print array elements with an average inter-element spacing of 130 µm or less, 100 µm or less, 90 µm or less or 70 µm or less.

In certain embodiments the microarray printer utilizes pressure and vacuum to control reagent loading or dispensing. In certain embodiments where the spotting capillaries are in fluid communication with a manifold thereby permitting liquids to be drawn through the capillaries into the manifold. In certain embodiments the manifold comprises a common port and individual ports where an aperture into an individual port is disposed inward of the inside wall of the manifold. In certain embodiments the device can print more than 200 microarray substrates in a run. In certain embodiments the device loads reagents from a microtiter plate comprising at least about 300, 864, or at least about 1536 wells. In certain embodiments the device comprises means for applying positive or negative pressure to the spotting capillaries and/or to the vacuum chamber in the print head.

In another embodiment this invention provides a platen for positioning a substrate holder or a print head in a microarray printing device. A preferred platen comprises a support surface attached to a single guide rail such that the support surface can move along the guide rail, and motion of the support is constrained in a direction normal to the guide rail, and a flexible coupling to an actuator wherein the flexible coupling is rigid or stiff in a direction parallel to the guide rail, but is flexible in another direction. The platen also, optionally, comprises an encoder (e.g. optical encoder, magnetic encoder, electronic encoder, etc.) that encodes the position of said platen along said guide rail. In certain embodiments, the platen is attached to the rail by two bearings. Preferred flexible couplings include, but are not limited to a flexible sheet coupling (e.g. sheet metal, sheet plastic, etc.), a rod bearing, a ball bearing, a pin bearing and the like. Preferred actuators include, but are not limited to a stepping motor, a linear motor, a lead screw, and the like. In certain embodiments, the platen can further comprise a holder (e.g. a slide holder) for one or more microarray substrates. In certain embodiments, the platen is attached to a microarray print head (e.g. directly or through a movable stage). Preferred print heads in such cases include, but are not limited to any of the print heads described herein.

In still another embodiment, this invention provides a microarray printing device comprising a microarray print head (e.g. as described herein); and a microarray substrate holder attached to a platen (e.g. a platen as described herein). Preferred microarray printers can print at least 2,000, more preferably at least 5,000 array elements per spotting capillary per load. Preferred microarray printers can print array elements with a precision of at least 30 µm and/or with an average inter-element spacing of 130 µm or less. Preferred microarray printers can print 200 or more microarray substrates in a run. Particularly preferred microarray printers of this invention utilize pressure and/or vacuum to control reagent loading or dispensing. Certain microarray printers comprise the spotting capillaries are in fluid communication with a manifold. A preferred manifold comprises a common port and individual ports where an aperture into an individual port is disposed inward of the inside wall of the manifold. In certain preferred embodiments, the microarray printing device can loads reagents from a microtiter plate comprising at least about 864 wells.

This invention also provides a method of printing a microarray (e.g., a nucleic acid and/or protein and/or small organic molecule microarray). The methods involve providing an array substrate in a microarray printing device comprising one or more of the elements (e.g. spotting capillaries, print head, array substrate platen, print head platen, and the like) as described herein, providing a series of solutions comprising the reagents that will form features of the microarray; and operating said microarray printing device to print the microarray. In preferred methods the microarray printing device prints a microarray comprising at least 1,000 different array elements. In preferred methods the microarray printing device prints a microarray comprising having an average inter-feature spacing of about 130 μm or less. Preferred array substrates include, glass, quartz or other minerals, metals, ceramics, plastics, metal coated glass, metal coated plastic and the like. In preferred methods the microarray printing device applies negative pressure to load a spotting capillary and/or positive pressure to dispense from a spotting capillary. In preferred embodiments, the method involves loading feature-forming reagents from a microtiter plate comprising at least about 864 wells.

In still another embodiment, this invention provides (printed) microarrays. Preferred printed microarrays comprise at least about 1000 different array elements on an array substrate, where the array elements are separated by an average center to center spacing of about 130 μm or less, preferably about 100 μm or less, more preferably about 80 μm or less. Where the arrays are nucleic acid and/or protein arrays, the protein or said nucleic acid is preferably not a chemically synthesized protein or nucleic acid. Particularly preferred microarrays include nucleic acid nucleic acid microarrays. In certain embodiments, the nucleic acids comprising such microarrays have an average length greater than about 50, preferably greater than about 100, 200, or 500 nucleotides, more preferably greater than about 1000 nucleotides. The molecules comprising the array features are preferably adsorbed to the array substrate. In certain nucleic acid or protein arrays the nucleic acid or protein is not covalently coupled to the array substrate (e.g. not coupled directly or though a linker to a terminal nucleotide or amino acid). In particularly preferred microarrays, the features comprising the arrays are at an average density of about 40,000/cm$^2$ or greater.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235, 033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev. pp* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "spotting capillary" and "pin" or "printing pin" are used synonymously to refer to the structure that is used to contact a microarray substrate and thereby deposit a reagent to form a microarray feature on that substrate. Unlike many printing pins, however, the spotting capillary is typically a tube and, while not limited to such, in certain preferred embodiments, display a round cross section.

The term "coupled to" when used with reference to a capillary or capillaries coupled to a piston indicates that the piston(s) are coupled to the capillary or capillaries such that movement of the capillary with respect to the print head in a direction along the longitudinal axis of the capillary requires movement of the piston(s).

The term "fixed spacing" when used with respect to capillaries in a print head indicates that the capillaries maintain a fixed location (laterally) with respect to each other. While in certain embodiments, the spacing can be regular, it need not be so.

The term "accommodates" when used with reference to spacing of capillaries accommodating a microtitre plate indicates that the capillaries are spaced such that each capillary can be placed in a separate well in the microtitre plate at the same time. Standard microtitre plates include, but are not limited to 96, 384, 864, and 1536 well plates.

A "substrate holder" refers to a means for temporarily restraining one or more substrates on a platen during a microarray printing operation so that the substrates don't significantly move with respect to the platten during that printing operation. Microarray substrate holders include, but are not limited to certain adhesives, clips, spring retainers, vacuum ports, and the like.

An "array substrate" refers to the surface or support on which a microarray is printed. Array substrates include, but are not limited to glass, quartz or other minerals, ceramic, porcelain, metal, and metal-coated glass.

An "array feature" or "array spot" refers to a reagent or reagents deposited at a location on an array surface. Typically a feature is characterized by the presence of one or more specific molecules (e.g. particular proteins, nucleic acids, etc.).

A "guide rail" refers to a rail or other device that directs or orients the movement of a platen as described herein. In certain embodiments, guide rail can take any of a number of forms including, but not limited to T-shaped, round, triangular, square, ovoid, and the like. The guide rail is typically coupled to the platen through one or more bearings that permit motion of the platen in one direction (along one axis), but restrict motion in other directions. In certain preferred embodiments, the guide rail is configured to control the motion each degree of freedom of the spotter (e.g. the platten and/or print head) the parts of the robot with the minimal number of restraints that are required by Euclidian geometry, e.g. as described herein.

A "print cycle" refers to the sequence of events involved in printing an array feature.

The term "microarray" refers to an array comprising at least about 10, preferably at least about 50, more preferably at least about 100, still more preferably at least about 500 or 1000, and most preferably at least about 10,000, 40,000, 100,000, or 1,000,000 different and distinct features. Preferred microarrays have an average feature density greater than about 100/cm$^2$, more preferably greater than about 1000/cm$^2$, still more preferably greater than about 5,000/cm$^2$, even still more preferably greater than about 10,000/cm$^2$, and most preferably greater than about 20,000/cm$^2$, 40,000/cm$^2$, 60,000/cm$^2$, or even 80,000 cm$^2$.

BRIEF DESCRIPTION OF THE DRAWINGS

FIG. 1A illustrates a print head 10 comprising a series of guide plates 14 that support and position the spotting capillaries 12. The downward motion of the spotting capillaries is limited by a detent 20 and the spotting capillaries are returned to the "extended" position by a spring 18 compressed between the detent and a spring capture plate 22. The spotting capillaries communicate to a manifold through a flexible capillary tubing 24. FIG. 1B illustrates a print head capable of mounting 64 spotting capillaries on 3 mm centers for 864 well microtiter plates. In this illustration, 16 spotting capillaries are in use.

as illustrated in FIG. 15) reduces capillary flexion in increases precision in spot placement on the substrate. Close tolerances on holes limit vacuum leakage and constrain pins.

DETAILED DESCRIPTION

Figure 1A:
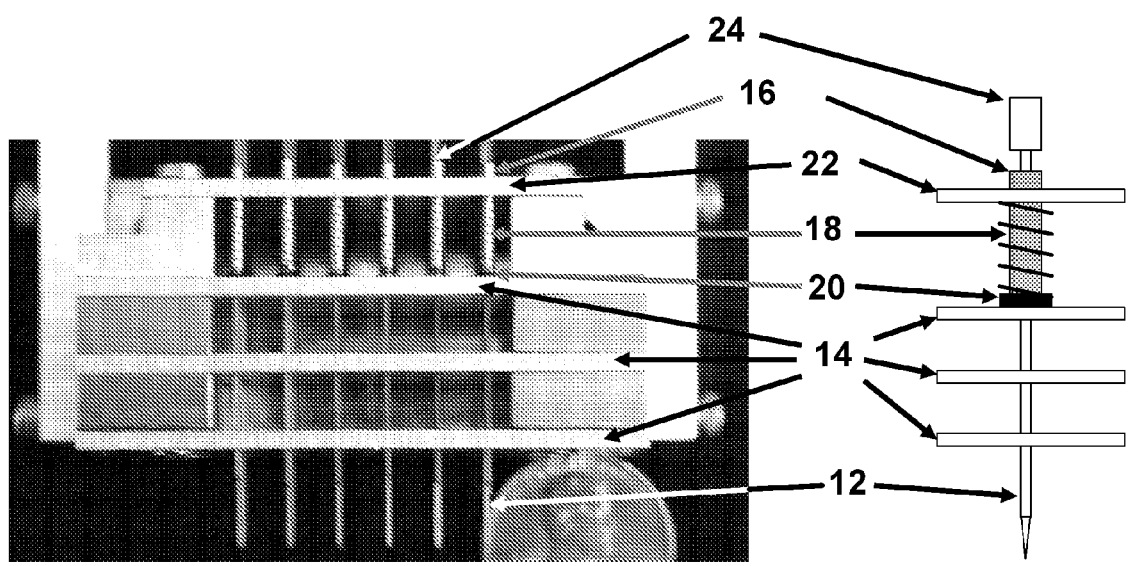
FIGS. 1A and 1B illustrates a microarray printer print head 10 of this invention.

This invention pertains to a microarray printer that can be used to manufacture microarrays (e.g. of biochemical samples) by direct contact printing. The array printer of this invention is capable of printing microarrays at higher feature density, with greater speed and lower cost than previous microarray printing devices.

Without being bound to a particular theory, these efficiencies are achieved by the use of a combination of novel features. A novel printing pin permits vastly more efficient reagent usage and a greater number features to be printed per load. This reduces reagent costs, and because the pin does not require repeated refills during the printing process, the printing operation proceeds more rapidly.

In addition, positive control of reagent flow using pressure and vacuum, also improves reagent capture and delivery and reduces the incidents of mis-prints due to pin blockage during loads or print steps. In addition, positive pressure control keeps the liquid at the tip of the printing capillary. This significantly improves printing reliability.

A novel design for the substrate support permits the use of a larger positioning substrate that can hold a greater number of array substrates (e.g. more than 10, preferably more than 20 or 50, still more preferably greater than 100, and most preferably greater than 150, 200, 250, 300, or even greater than about 500 standard slide-sized substrates) and position each array with greater accuracy and precision. The substrate support is kinematically constrained so that printing substrates are more reproducibly positioned even at rapid accelerations and decelerations, thereby permitting a print run to proceed with greater rapidity, i.e., decreasing effective print time and reducing printing costs, and to print arrays with a higher density of spots.

A related kinematic support design for the print head permit rapid acceleration and deceleration of the print head and reproducible positioning. The rapid precise positioning of the array substrate combined with the rapid positioning of the print head again, significantly reduces the time required for a print cycle thereby reducing costs, and increases the utility of the arrays by allowing production of a higher density of spots.

These features combine to make possible the efficient printing of microarrays at extremely high efficiency with low reagent usage, and previously unobtainable feature spacing for printed microarrays.

I. Printing Pins and the Print Head.

In one embodiment, this invention provides for print head 10 for printing microarrays and a microarray printer comprising such a print head. As illustrated in FIG. 1, in one preferred embodiment, the print head 10 comprises a plurality of spotting capillaries 12 disposed in a support 14 that maintains a fixed spacing between the spotting capillaries and that permits the spotting capillaries to move in a direction parallel to the long axis of said capillaries (i.e., the spotting capillaries can slide in the support).

The spotting capillaries 12 are preferably cylinders (e.g. capillary tubes) made of a rigid material such as glass, quartz or other mineral, ceramic, brittle plastic (e.g. acrylic), and the like. It was a surprising discovery of this invention that glass-like materials such as glass or quartz or ceramic could be effectively used as spotting capillaries. Moreover, particularly when fabricated and utilized as described herein, such glass, quartz or ceramic spotting capillaries have a useful lifetime vastly greater than that observed for the commonly utilized metal pins. Indeed, we have yet to determine the maximum lifetime of the spotting capillaries described herein, while it is believed that metal spotting are quite limited in their useful life.

Figure 2:
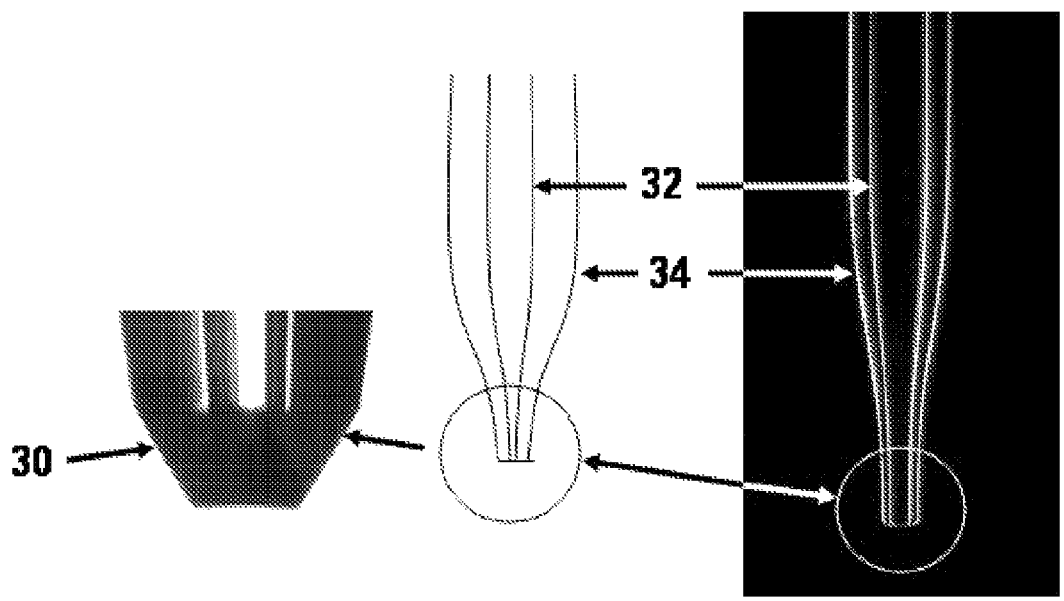
FIG. 2 illustrates a glass or quartz spotting capillary of this invention showing the inside diameter 32, the outside diameter 34, and the bevel 30 at the tip.

The spotting capillaries used in this invention can be of any convenient size, however, in preferred embodiments (see, e.g., FIG. 2), the spotting capillaries are microcapillaries, with an inside diameter (bore width) at the tip of less than about 100 µm, preferably less than about 75 µm, more preferably less than about 50 µm, and most preferably less than about 30 µm, 25 µm or even less than about 20 µm. The lower size limit (bore diameter) can be determined by practical considerations of plugging given the occurrence of particulate matter in some preparations. Thus, there can be practical size limits on the printing capillary tip opening size given the care (cleanliness) with which the printing solutions are prepared. If the inside diameter of the capillary is too small and the capillary is too long, then the flow resistances of the capillary can impede the ability to rapidly draw cleaning solutions etc. through it. Thus, in certain preferred embodiments, the capillaries are used that have a larger ID away from the tip, and the capillary diameter (ID and OD) is reduced at the tip to produce a small feature (spot) size. The load volume (loaded fluid volume) of the spotting capillary is typically 1 µL or less, preferably 0.5 µL or less, more preferably 0.25 µL or less, and most preferably 0.2 µL or less or even 0.1 µL or less.

As indicated above, the spotting capillaries need not have a constant internal diameter. The diameter (ID and especially OD) at the aperture (spotting face) of the spotting capillary will, in part, determine the minimum feature size of the spotted microarray. Thus, smaller aperture and external tip diameters are preferred. Particularly preferred aperture diameters (ID or OD) are less than about 75 µm, more preferably less than about 50 µm, and most preferably less than about 30 µm, 25 µm or even less than about 20 µm or 15 µm. In certain embodiments, the diameter of the internal channel expands to a maximum of about 100 µm, preferably about 75 µm, more preferably about 50 µm. In one embodiment, illustrated in FIG. 2, the spotting capillary has an aperture diameter of about 30 µm or less and a maximum internal diameter of about 75 µm or less. The capillary holds about 0.2 µL or less, preferably about 0.1 µL or less.

The spotting capillary outer diameter determines the minimum inter-pin (inter-capillary) spacing, and the inter-pin spacing determines the minimum spacing of the reservoir(s) from which the print head can load reagents. Preferred spotting pins have an outside diameter of about 1 mm or less, more preferably of about 0.7 mm or less, and most preferably of about 0.4 mm or less. The 0.4 mm spotting capillaries can be mounted very close together and, with such close spacing, the print head can load reagents from standard 96 well, 384, well, 864 well, and 1536 well microtiter plates. In preferred embodiments, the center to center spacing of the spotting capillaries is about 10 mm or less, preferably about 5 mm or less, more preferably about 3 mm or less, and most preferably about 2 mm or even 1 mm or less. Such close spotting capillary spacing can be achieved, e.g. using the print head designs illustrated herein, allowing the use of even higher density sample reservoirs.

The support(s) for the spotting capillaries can take any of a number of a number of forms. For example, in one embodiment, the support can comprise a number of channels drilled, etched, or cast in a single metal or plastic piece. The channels then act as guides for the spotting capillaries. Alternatively, the support can be fabricated as by joining a collection of tubes e.g. metal tubes. The tubes can be glued or welded together to form a single support structure, each of the tubes acting as a channel for housing a spotting capillary.

In a particularly preferred embodiment, as illustrated in FIG. 1A, the spotting capillaries are supported and positioned by a series of guide plates 14, and optionally, by a guide cylinder 16. To prevent breakage of the spotting capillaries e.g., do to the repetitive contacting with the printing substrate, the spotting capillaries are capable of sliding through the guide plates, e.g. when they contact the spotting substrate. The spotting capillaries are then returned to their "extended" position by a spring 18.

While FIG. 1A is illustrated with a coiled spring, it will be appreciated that any of a variety of springs can be used. These include, but are not limited to deformable elastic masses, deformable elastic membranes, "rubber bands", air pressure, and the like.

The extended position of the spotting capillaries is limited by a detent 20. The detent can take any convenient form. For example, the detent could comprise a set screw (preferably plastic so as not to damage the spotting capillary), a drop of epoxy or other resin, and the like. In one particularly preferred embodiment, the detent is a disk attached to the spotting capillary. In one embodiment the detent stops up against the pin guide plate The "downward" extent of the spotting capillary can be determined by the position of attachment of the detent to the spotting capillary. Alternatively, the guide plate can further comprise an adjustment means (e.g. a set screw, a shim, etc.) for each spotting capillary that can be used to adjust the downward travel for each spotting capillary.

In certain embodiments, the spring typically rests against a resisting surface, e.g. a spring capture plate 22.

It was also a discovery of this invention that spotting capillaries, particularly when fabricated of glass, quartz, other minerals, or ceramic or porcelain, show a dramatically improved lifetime, when the outer edges of the spotting tip of the spotting capillary, are not flush with the spotting face. Thus, in preferred embodiments, the outer edge of the spotting tip is beveled (see, e.g., 30 in FIG. 2).

Figure 1B:
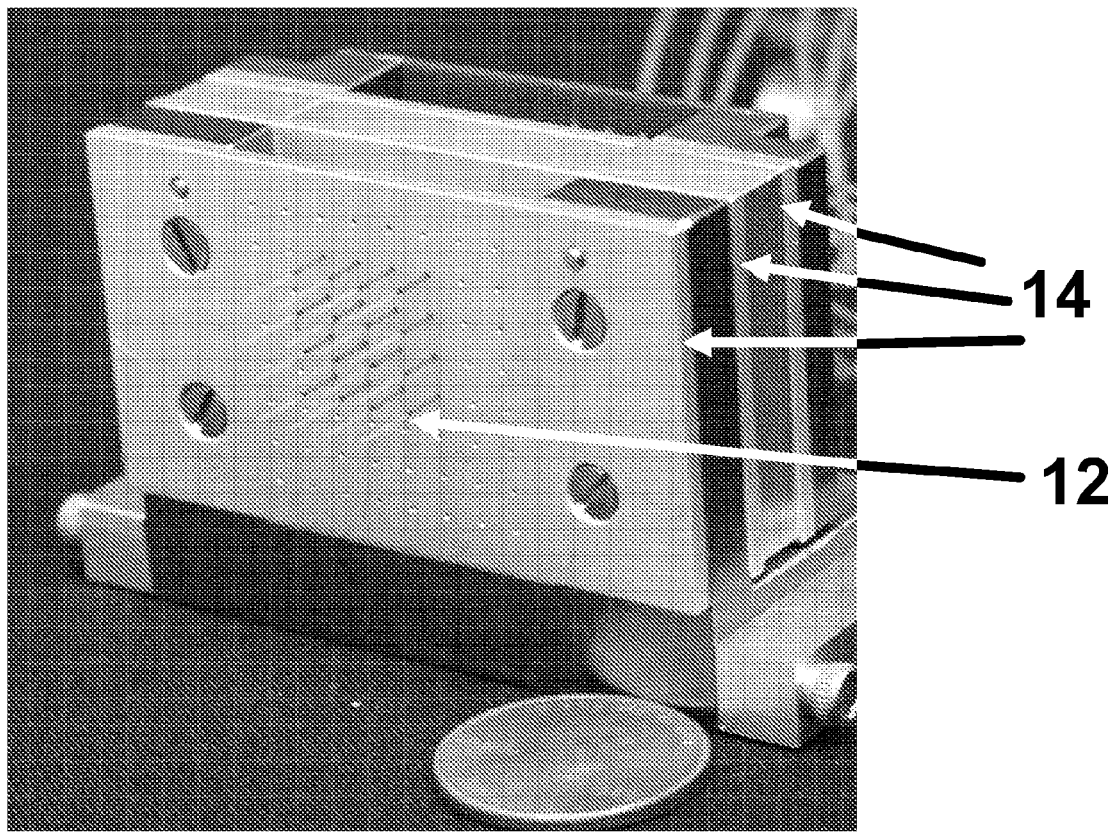

The print head typically comprises a plurality of spotting capillaries. Preferred print heads comprise at least two spotting capillaries, more preferably at lest 4 spotting capillaries, still more preferably at least 8 or at least 16 spotting capillaries, and most preferably at least 32. 64, 128, or 256 spotting capillaries. Depending on the application, a print head can be configured to use fewer than the maximum number of available spotting capillaries. FIG. 1B illustrates a print head capable of mounting 64 pins on 3 mm centers for 864 well microtiter plates. In this instance, 16 pins are in use.

The print heads of this invention can be fabricated using standard machining and glass handling techniques well known to those of skill in the art. The spotting capillaries are preferably fabricated by casting or by pulling a quartz or glass microcapillary tube using a commercially available microcapillary puller (e.g. Sutter Instrument P-2000 Capillary Puller). In particularly preferred embodiments, the microcapillary tip is then beveled using a glass grinder. Such spotting capillaries can be made to order by commercial production houses.

II. Magnetic Control of Printing Pins/Capillaries.

In certain embodiments, the printing capillary position can be controlled by magnetic methods. Both passive and magnetic control methods are contemplated by this invention.

A) Passive Magnetic Control of Printing Pins/Capillaries.

Figure 13:
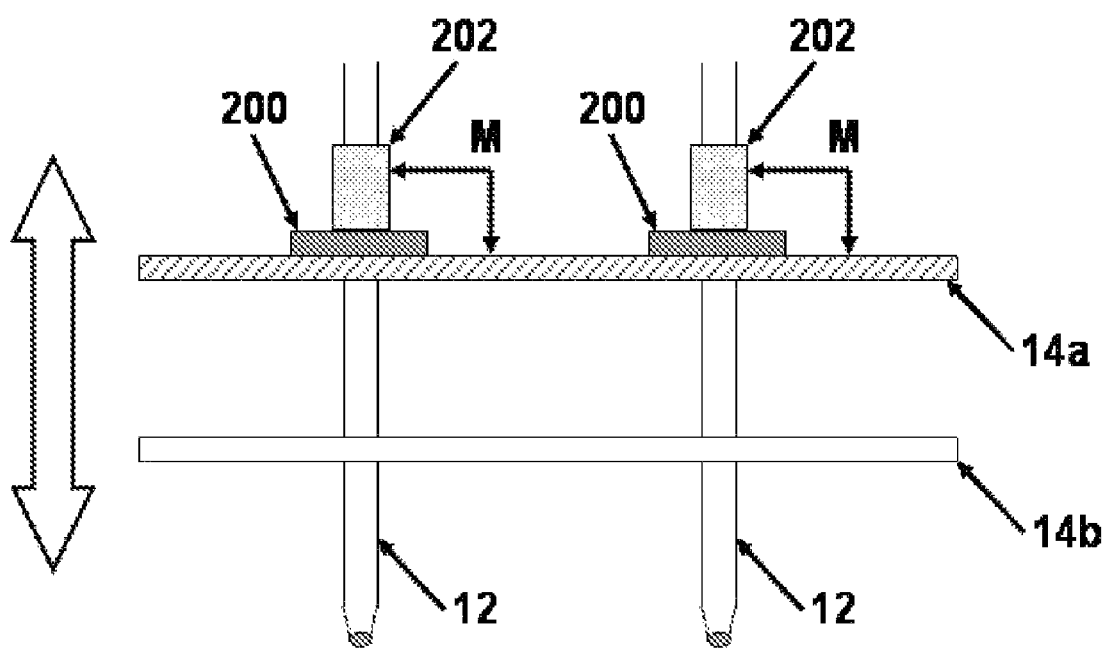
FIG. 13 illustrates a scheme for passive magnetic control of printing pin/capillary position.

A passive magnetic control system is schematically illustrated in FIG. 13. This figure illustrates a portion of a print head comprising a printing capillary 12 and guide plates 14a and 14b. The capillaries have affixed thereto a magnetic material 202. Similarly, guide plate 14a can be a magnetic material. One or both of 202 and 14a is magnetic and a "passive" magnetic attraction "M" pulls the capillary 12 downwards. The downward travel of the capillary is stopped by optional spacer 200.

The open arrow indicates the direction of motion of the print head during a printing operation. When the print head is lowered, the printing capillaries contact the array substrate. The are then no longer held down by the magnetic force "M". When the print head is raised, the magnetic attraction between 200 and 14a pulls the pins/capillaries back to the reference position. This system makes is easy to change printing pins. They can be changed just by pulling them out of the top of the print head.

B) Active Magnetic Control of Printing Pins/Capillaries.

Figure 14:
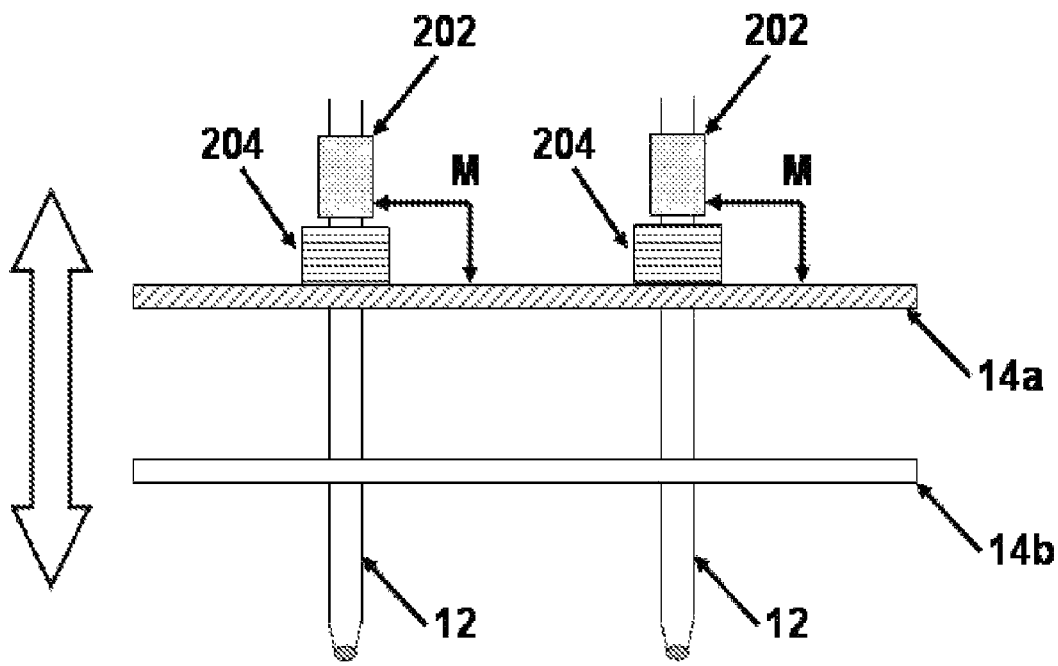
FIG. 14 illustrates a scheme for active magnetic control of printing pin/capillary position.

An active magnetic control system is schematically illustrated in FIG. 14. In this embodiment, the printing pins are contacted with the array substrate using electromagnetic means. The system offers two advantages. First, the printing pins move, while the print head remains stationary, so printing speed is increased. Second, the printing pins can readily be changed, simply by lifting them out of the top of the print head.

In this embodiment, guide plate 14a is an electromagnet. Each printing pin/capillary has affixed thereto a material 202 that is attracted by a magnetic field (e.g. a ferrous material, a magnet, etc.). A spring or elastic material 204 lifts the pins when the electromagnet is not activated. When the electromagnet 14a is activated, the pins are drawn downward to contact the array substrate thereby depositing array features.

The system is simple to build since only one electromagnet is required regardless of the number of pins/capillaries.

III. Vacuum Control of Printing Pins/Capillaries.

Figure 15:
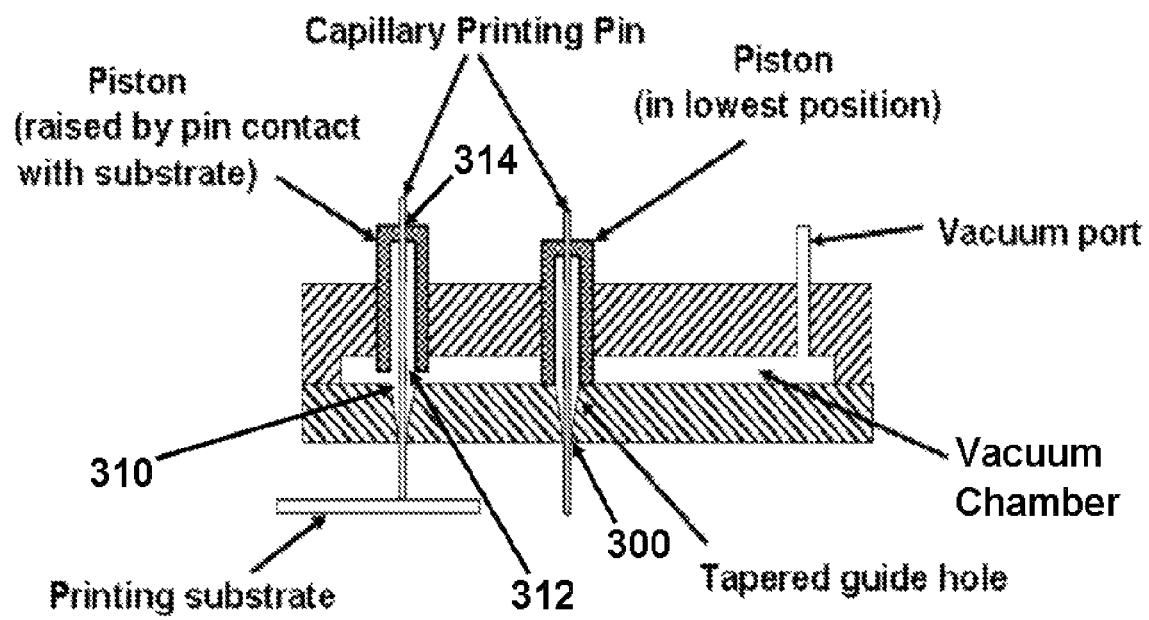
FIG. 15 illustrates one embodiment of a vacuum print head of this invention. As illustrated here, the print head comprises a chamber (vacuum chamber) having a bottom that comprises a plurality of tapered guide holes to accommodate the spotting capillaries/pins. The tapered guide holes end in high precision holes 300 that accurately position the capillaries, while the large opening 310 at the top of the guide holes allows easy insertion and accurate alignment of pins/capillaries. By providing a comparatively large opening 312 at the bottom of the piston(s) and attaching or otherwise restraining the capillarie(s) at the top or upper portion 314 of the piston allows the pins or capillaries to flex and to relieve binding that might occur due to close manufacturing tolerances.

In certain embodiments, this invention provides print heads permit control of spotting pin/capillary movement by a vacuum. One embodiment of such a system is schematically illustrated in FIG. 15. In this embodiment, the spotting pins/capillaries are attached to pistons that are disposed in a chamber, e.g., as shown. The pistons penetrate one side of the vacuum chamber and capillaries penetrate the pistons and the opposite side of the chamber after passing through a gap in the interior face of the piston.

The spotting pins/capillaries can be loaded and removed from the top of the device. Tapered guide hole in the bottom of the chamber ending in high precision holes, and allow easy insertion and accurate alignment of pins. Attaching the spotting pins/capillaries to the tops of the pistons allows the flexibility of the pins/capillaries to relieve binding that might occur due to manufacturing tolerances. Close tolerances on the holes limit vacuum leakage. Adjustment of vacuum allows regulation of the force on the pins/capillaries to minimize loads on impact with the substrate.

Figure 16:
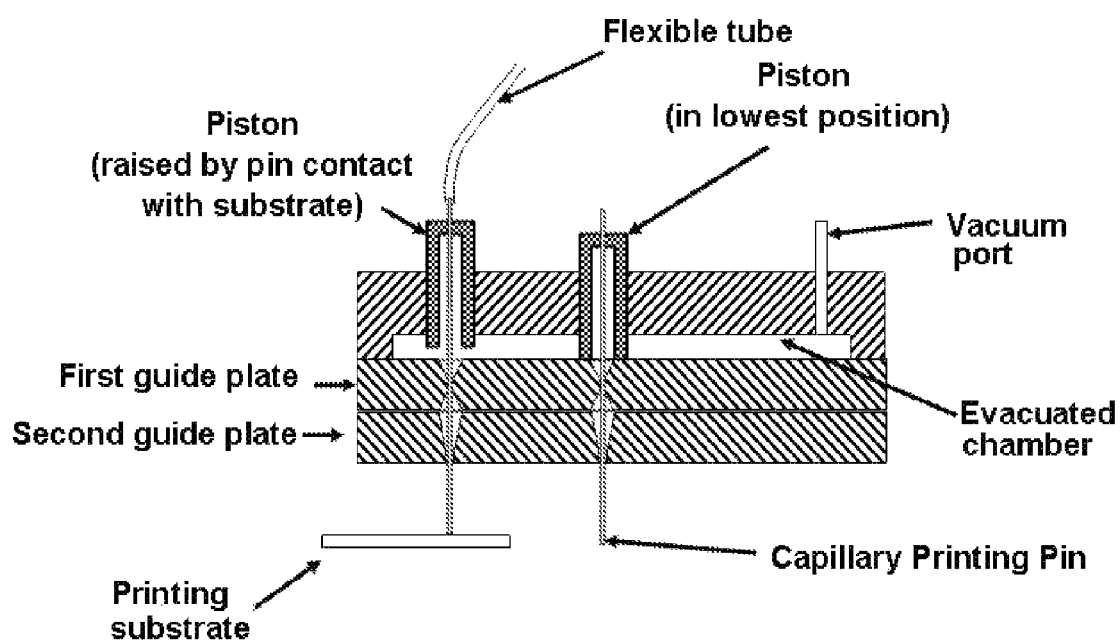
FIG. 16 Illustrates another embodiment, where tapered guide holes 318, end in high precision holes 300 (for accurate pin/capillary alignment) and allow easy insertion and removal/replacement of spotting pins/capillaries. The spotting pins/capillaries are constrained at three or more locations A (piston, first guide plate, and second guide plate) so that lateral forces from the flexible tubing connecting to the manifold, which may slightly bend the upper part of the pins/capillaries, does not cause significant deflection of the spotting pin/capillary tip. Three constraints (as opposed to two, e.g.

Another embodiment is illustrated in FIG. 16. In this embodiment, the bottom of the chamber comprises two guide plates both with tapered guide holes. The tapered guide holes, end in high precision holes (for accurate pin/capillary alignment) and allow easy insertion and removal/replacement of spotting pins/capillaries. The spotting pins/capillaries are constrained at three or more locations (piston, first guide plate, and second guide plate) so that lateral forces from the flexible tubing connecting to the manifold, which may slightly bend the upper part of the pins/capillaries, does not cause significant deflection of the spotting pin/capillary tip. Constraint at only two locations results reduced precision in spot placement due to pin bending. Close tolerances on holes limit vacuum leakage and constrain pins. Adjustment of vacuum allows controlling force on pins to minimize loads on impact with substrate. We have built print heads for 864 and 96, 384 and 1536 well standard plate formats. Careful manufacture of the tips, coupled with attachment of the pins to the pistons in an alignment jig, results in maintaining of spotting precision even if pins rotate during operation or are replaced during a print run. Pin rotation can be restrained if desired.

IV. Platens for Array Substrate and/or Print Head Positioning

To reliably print an array at high feature density (spots/cm$^2$) it is desirable to reliably and consistently position the spotting capillaries on the microarray substrate. The more precisely and consistently the print head can be positioned relative to the microarray substrate(s), the more possible it becomes to print arrays at a higher feature density.

Figure 3:
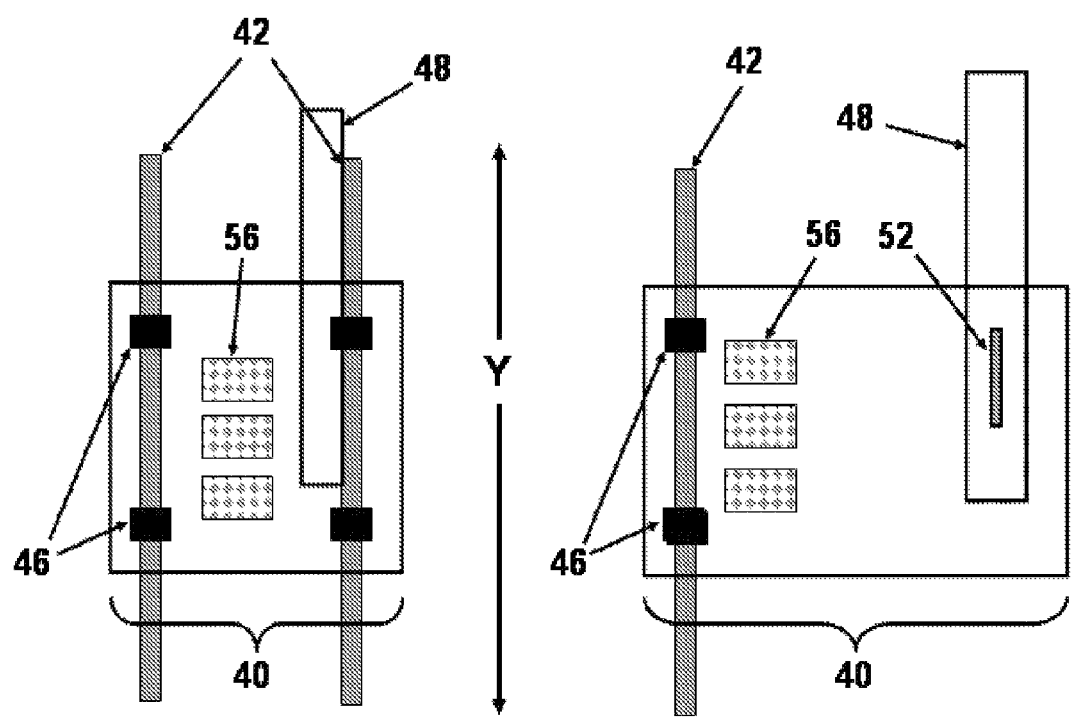
FIG. 3 illustrates a two-rail positioning platen compared to a preferred one-rail platen.

Printing a larger number of arrays at a time, however, requires a larger array substrate support (platen). The larger the platen, the more difficult it becomes to reliably and consistently position it relative to print head. One approach to solve this problem is illustrated in FIG. 3. The platen illustrated on the left utilizes two guide rails 42 to minimize torque and yaw and hysteresis of the platen introduced by the actuator which moves the platen, e.g. in the ±Y direction. To accurately print arrays, it is desirable to accurately position the platen to tolerances better than 50 µm. Such precise positioning requires extremely good bearing alignment for the four bearings and the guide rails must be extremely parallel. The rails and bearings must stay aligned throughout the printing operation. One of skill in the art will appreciate that such a device will tend to jam and/or introduce positioning imprecision as the actuator drives the platen through jammed positions if the alignment is not adequate. Leaving "play" in the bearings to allow motion results in positional imprecision. In still other standard types of arrayers the guide rails, e.g. as illustrated in the embodiment on the left in FIG. 3 are incorporated into the actuator. These rails are closely spaced and permit slight random yaw motions of the platen. For large platens, even this slight yaw results in a positional uncertainty that increases as one moves away from the center of the platen and decreases array element accuracy and therefore array element density.

Such difficulties are solved with the platens of this invention. One embodiment of a platen 40 of this invention is illustrated by the platen on the right in FIG. 3, and in FIG. 4. In certain embodiments, the plattens of this invention utilizes a single guide rail 42 to constrain the position of the support surface 44 that bears the array substrates 56. The guide rail is typically coupled to the platen through one or more bearings that permit motion of the platen in one direction (along one axis), but restrict motion in other directions. In certain preferred embodiments, the guide rail/platten configuration is designed to control the motion each degree of freedom of the spotter (e.g. the platten and/or print head) with the minimal number of restraints that are required by Euclidian geometry. Thus, for example, two points determine a line, three points determine a plane etc. To limit degrees of freedom around the guide rail, two coupling points (e.g. bearings) are used to constrain the direction of motion (e.g. in a line), and a coupling point is used at a location off of the line to limit the degrees of freedom of the platten, a plane. The attachment to this third point provides some flexibility in certain degrees of freedom etc. since the guide rail may not be accurately straight. In this example, it is not desired to place three bearings on the guide rail since that is more than required and if the rail is slightly curved the bearings will bind. Similarly one bearing on the rail is generally insufficient, because that will allow the platten to rotate.

Figure 4:
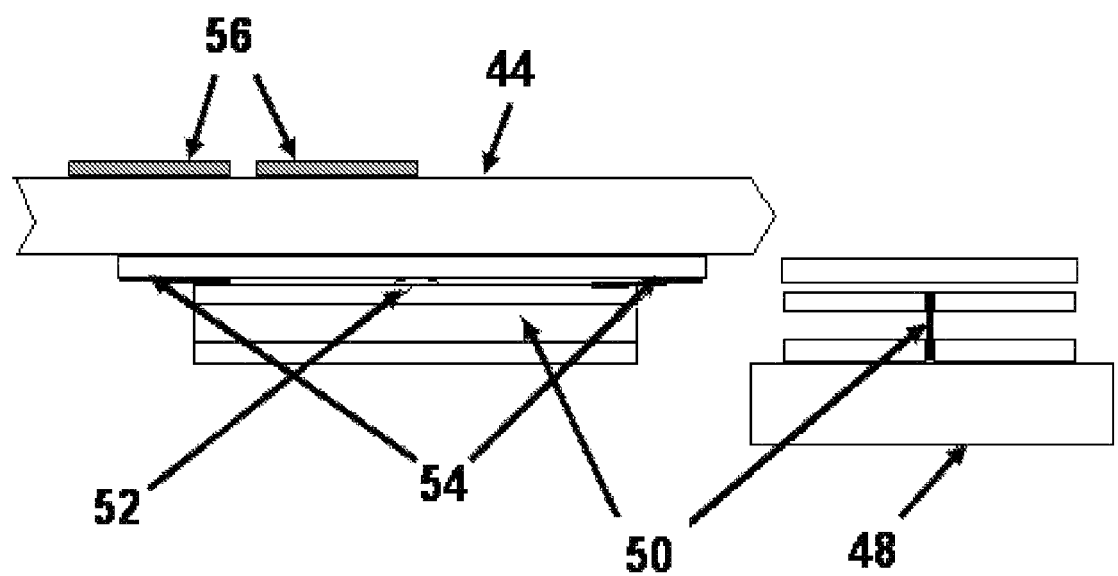
FIG. 4 illustrates one embodiment of a platen used to position an array substrate in an array printing device.

Illustrative embodiments, of these principles are provided in FIG. 3, and in FIG. 4. As illustrated, the platen utilizes a single guide rail 42 to constrain the position of the support surface 44 that bears the array substrates 56. The support surface communicates with a guide rail 42 through two bearings 46, the minimal number required to define linear motion. The support surface is coupled to an actuator 48 through a flexible coupling 50.

The bearing(s) 46 and the guide rail 42 prevent the platten (e.g., the support surface) from yawing in response to a force created by the actuator. However, because there is only a single rail, there are no difficult alignment problems. Straightness of the guide rail is also not critical because any rail deformation will be constant and reproducible, i.e., repeated positioning of the array substrates will be consistent, and the bearings will not bind due to possible curvature in the rail. An encoder 58 accurately encodes the location of the platen. The encoder can be external to the actuator as shown in the drawing, or it can be built into the actuator as is common in commercially available actuators.

The support surface is coupled to the actuator through a flexible coupling 50 that is rigid in the direction of travel (±Y direction in FIG. 3), but compliant in all other directions. This permits the actuator to accurately position the platen (e.g. in the Y direction as shown), while not jamming or binding in other directions.

The distance between the two bearings on the guide rail determines how much yaw motion will be permitted in the platten. If the bearings allow a certain lateral motion, that will be translated into a yaw of the platten. The positioning precision is related to the length and width of the slide platten in relation to the distance between the two bearings on the guide rail. It is desirable to provide very high reproducibility in the positioning of the plattens, but the absolute accuracy is not so critical. Thus if the guide rail is curved a bit, the platten will yaw as it moves, but that motion will be very reproducible so that the next array spot is printed, it is properly placed relative to the previous spots, although the entire array on one substrate will be positioned slightly differently than on a substrate at a different location on the platten. Thus the system is designed to give extremely good performance on the relative positions of spots in an array.

The embodiment illustrated in FIG. 4 allows slight motion in the X direction, and yaw, roll and pitch compliance. The system is stiff in the Y direction. One thing to note is that with the flexing, especially pitch, the locations on the platen will vary compared to the encoder, when the encoder is on the motor (actuator) carriage. As long as these variations are reproducible, then the positioning is reliable.

The flexible coupling 50 illustrated in FIG. 4 is a flexible sheet (e.g., sheet metal. This flexure gives freedom in yaw, roll and X, and is stiff in Y, the direction of platen travel. If pitch freedom is desired, it is possible to introduce additional flexible couplings 54. Alternatively, a bearing can be used. The two flexures 54 will be stiff in the Y direction as long as the platen does not lift up under acceleration, and will be stiff in yaw so that all of the yaw compliance will be taken care of in the vertical sheet.

In certain embodiments, a pivot 52 is provided. In various embodiments, the pivot 52 includes, but is not limited to two points across the width (into the drawing in the side view), a cylinder etc. In this design, pitch motion will require the upper mounting plate to slide across the pivot, so this is preferably lubricated and/or fabricated of low-friction materials, etc.

Figure 5:
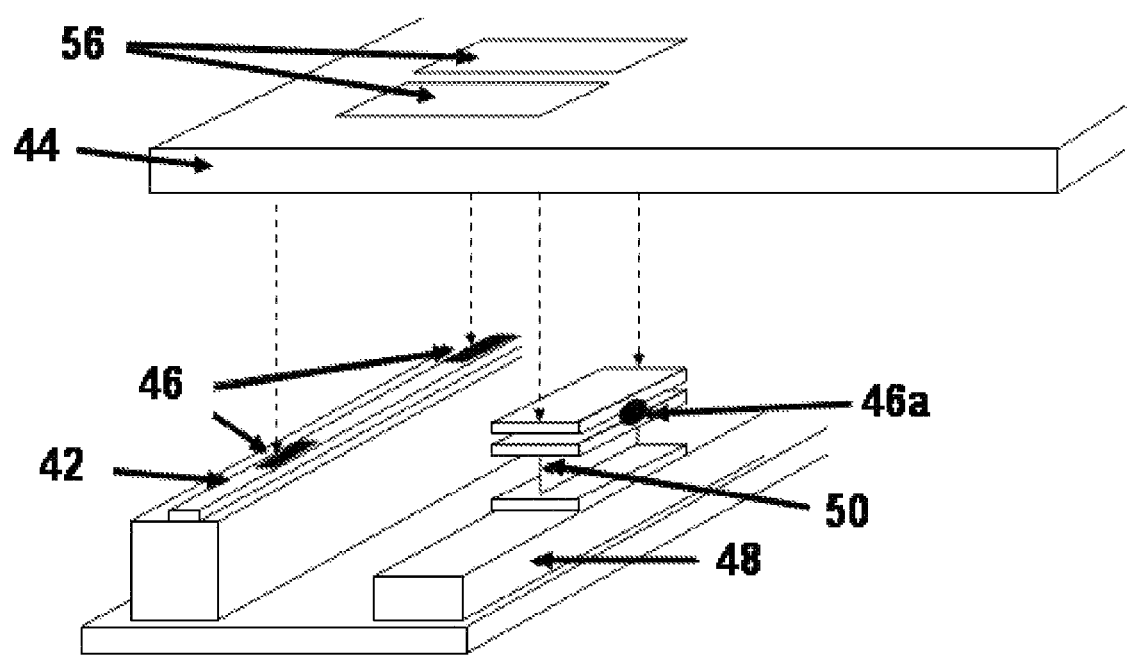
FIG. 5 illustrates an exploded view of a platen used to position an array substrate in an array printing device.

FIG. 5 illustrates one embodiment of an array substrate platen in an exploded view.

Figure 6:
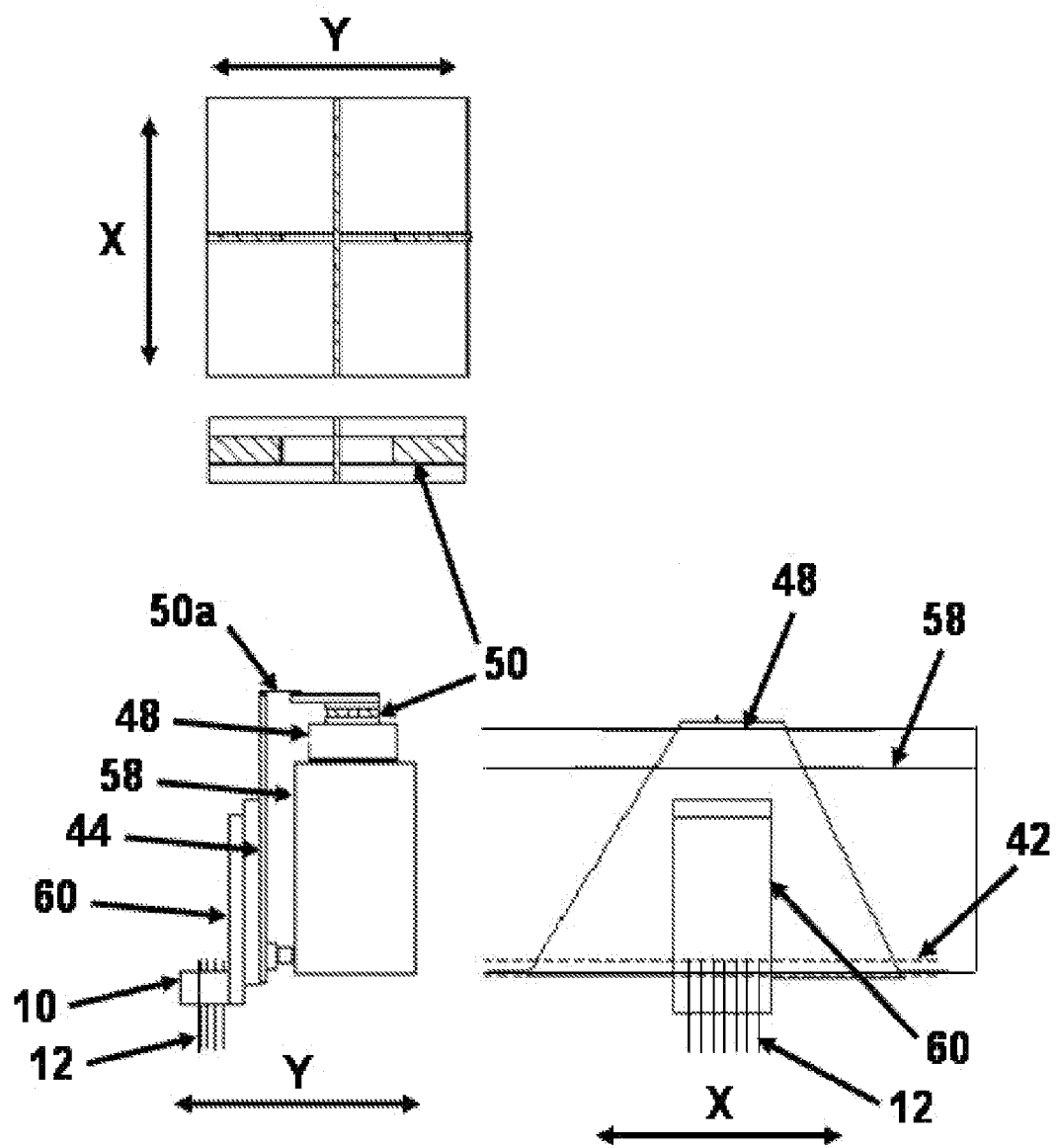
FIG. 6 illustrates one embodiment of a platen used to position a microarray print head in an array printing device.

FIG. 6 illustrates one embodiment of a platen used to move the print head in a microarray printer of this invention in a ±X direction (normal to the direction of motion of the array substrate platen). In this embodiment, the platen (support surface) is oriented vertically. A microarray print head 10 is attached to the support surface 44. In the embodiment illustrated in FIG. 5, the actuator 48 is a motor (e.g. a linear stepping motor). The actuator 48 is coupled to the support surface through a flexible coupling 50. The couplings are disposed such that deflection of the support surface is constrained (stiff) in the X direction (the direction of motion), and stiff in the Y direction, but compliant in yaw. The coupling 50a flexes to relieve Z, yaw, and roll of the platten. The platen rides along a truss 58 that bears a guide rail 42. In a preferred embodiment, the support surface 44 is trapezoidal in shape with the wide side of the trapezoid disposed along the guide rail. This permits the rail bearings to be widely separated and thereby minimize rotation of the support surface. Use of the trapezoidal shape minimizes support surface mass permitting more rapid acceleration and deceleration. The print head 10 is mounted on a Z stage 60 that controls vertical movement of the print head.

Because the moment arm between the flexible motor coupling 50 and the print head is large compared to the moment arm between the print head and the guide rail 42, rotations or deflections at the motor coupling have minimal effect on the position of the print head.

Using the teachings provided herein, one of skill would recognize numerous embodiments for the flexible couplings used in the platens of this invention. In certain embodiments, as indicated above, the flexible couplings comprise flexible sheets (e.g. sheets of metal, plastic, or other flexible material). The sheets are selected of materials that are stiff in tension, but capable of bending in other directions. Other flexible couplings include, but are not limited to ball bearings, rod bearings, pin bearings, and the like.

A wide range of encoders can be used to encode the position of the platen/support surface. Encoders are well known to those of skill in the art and include, but are not limited to optical encoders, mechanical encoders, magnetic encoders, and electronic encoders. Various electronic encoders include, but are not limited to encoders that convert the change in resistance of a potentiometer or the change in capacitance of a capacitor into a movement or position. Optical encoders include, but are not limited to encoders that convert an optical signal, e.g. a bar code, an interferometric measurement, etc. into a movement or position. Similarly, magnetic encoders include encoders that a change in magnetic flux or field into a movement or a position. Suitable encoders (e.g. with a positional accuracy greater than about 50 μm, preferably with a positional accuracy greater than about 25 μm, more preferably with a positional accuracy greater than about 10 μm, and most preferably with a positional accuracy greater than about 5 μm, greater than about 2 μm, or greater than about 1 μm are commercially available.

The actuator can be any device or means capable applying a force to the platens of this invention and driving them in a plus or minus direction along the guide rail. Suitable actuators include, but are not limited to stepping motors, linear induction motors, pneumatic actuators, solenoids, piezo-electric actuators, lead screws, and the like. Suitable actuators, and associated motion control products are commercially available from a wide variety of companies (see, e.g., Biorobotics (U.K), Parker Daedal, Irwin, Pa., and the like).

It is noted that in certain preferred embodiments, of the present invention, the slide support platen, with an encoder precision of about 2 μm achieves a spot (array element) precision of about 10 to about 20 μm at any array substrate location on the support surface. Particularly preferred platens achieve a spot (array element) precision of better than about 5 μm, more preferably better than about 2 μm, and most preferably better than about 1 μm, or 500 nm, or 200 nm at any array substrate location on the support surface.

Similarly, the print head positioning platen achieves a precision of about ±10 μm or less, more preferably about ±5 μm or less, and most preferably about ±3 μm or less over the entire slide (array substrate) support surface.

In certain embodiments microarray substrates are held on the platen using any of a variety of a microarray substrate holder(s). Such holders include, but are not limited to various adhesives on the platen and/or the substrate, retaining clips, wetting agents on the platen and/or the substrate, various vacuum operated substrate holder(s) and the like. In various embodiments the substrate holder utilizes a vacuum to prevent the substrate(s) from moving during a printing operation.

Figure 17:
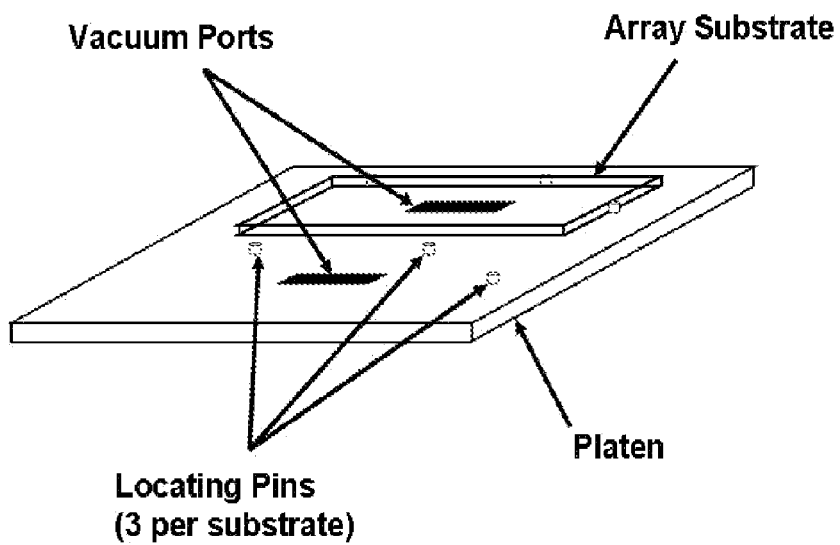
FIG. 17 illustrates a vacuum operated a microarray substrate holder.
Figure 18:
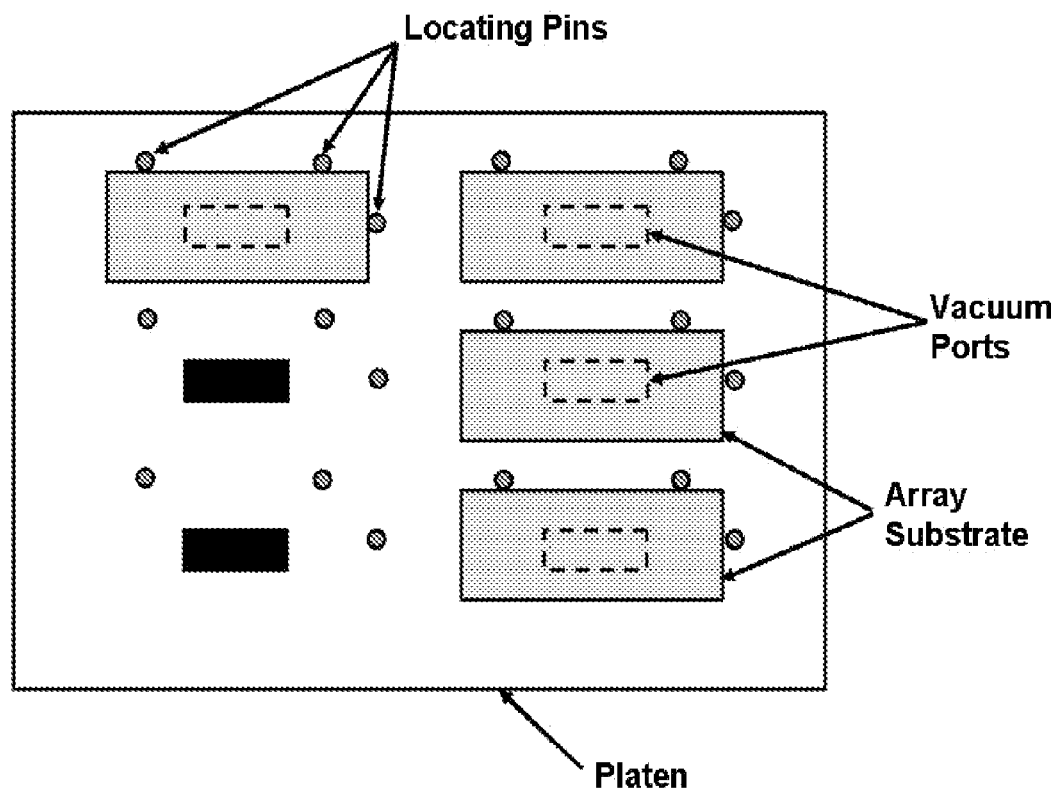
FIG. 18 illustrates a vacuum operated a microarray substrate holder.

One such vacuum-operated substrate holder is illustrated in FIGS. 17 and 18. As illustrated in these figures, pins are used to initially position the microarray substrate(s) on the platen. The pins position the substrates such that each substrate is placed over a vacuum port. Vacuum can then be applied to the port to fix the substrates in place during a printing operation. It will be appreciated that each port can be separately valved or groups of ports can be separately valved so the platen need not be filled with substrates during a printing run. Alternatively, if no valving is utilized to separately control the ports comprising the microarray substrate holder (s) then blank substrates or other materials can be used to block the unused ports.

V. Positive and Negative Pressure Control for Sample Loading and Dispensing.

A) Pressure Control Systems.

In a particularly preferred embodiment, the microarray printing devices of this invention utilize positive pressure and negative pressure (vacuum) to control sample loading and dispensing. Each "active" spotting capillary 12 is in fluid communication, e.g. via capillary tubing 70 with a manifold 64 (see, e.g., FIGS. 6, 7, 8, and 9) that permits the application of pressure or vacuum to the spotting capillaries.

Figure 7:
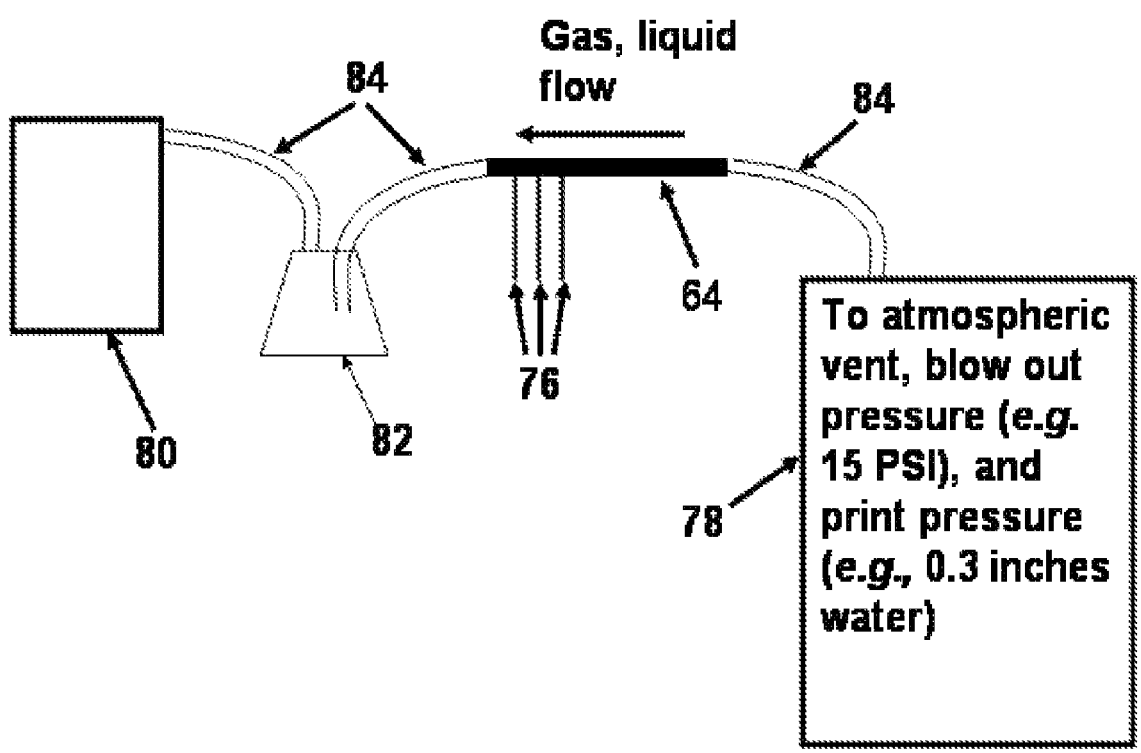
FIG. 7 schematically illustrates vacuum and pressure plumbing of a microarray printer of this invention.

A preferred plumbing scheme is illustrated in FIG. 7. In preferred embodiments, the gas flow (e.g. air, nitrogen, argon, etc.) flows through the manifold always in the same direction for all operations. This assures that any liquid drops that may be left in the tubing always will be forced to move toward the waste bottle and will not be blown back into the manifold. If droplets do get into the manifold they may block the supply of printing pressure to one or more pins, thus reducing the reliability of the printing.

In general, the plumbing system comprises a pressure source 78, and a vacuum source 80. The pressure and vacuum sources are in fluid communication with a manifold 64, e.g. via tubing 84. The manifold is also in fluid communication with the spotting capillaries so that pressure or vacuum applied to the manifold is delivered to the channel (bore) in the capillaries. In preferred embodiments, there is a waste receptacle disposed between the low vacuum source 80 and the manifold 74. In certain embodiments, vacuum source 80 supplies various levels of vacuum. —a "high" vacuum for cleaning and for starting the filling of the pins with a vacuum pulse, and a "low" vacuum that is sometimes used to help capillary action complete the filling of the pins. This low vacuum is typically low enough so that the printing liquid is not pulled past the top of the printing pins and into the flexible capillary tubing.

In preferred embodiments, the system is designed so that the tubing from the waste bottle to the manifold preferably slopes downward to facilitate liquid flow, and we strive to minimize the volume of the tubing and waste receptacle so that the pressure changes are transmitted to the manifold quickly. Thus, while the tubing communicating the pressure and vacuum to the manifold and communicating the manifold to the waste receptacle can be essentially any convenient tubing (as long as it is resistant to the reagents employed), in preferred embodiments, the tubing is a low void volume tubing (e.g. a fine bore capillary tubing), but the diameter is not so small as to introduce too much flow resistance. Such tubings are well known to those of skill in the art.

In one preferred embodiment the pressure source 78 can apply two pressures, a blowout pressure (e.g. 15 PSI), and a positive pressure used during printing (e.g. from about 0.1 to 2, preferably from about 0.1 to 1, more preferably from about 0.1 to about 0.5, and most preferably about 0.3 inches of water). Similarly, in preferred embodiments, the vacuum source 80, can apply two pressures, a "high vacuum" for cleaning, and for starting filling of the tubes using a short burst of vacuum, and a "low vacuum" to assist capillary action in filling the printing pins. The waste receptacle is preferably a low volume waste receptacle (e.g. a 200 ml waste bottle).

Figure 8:
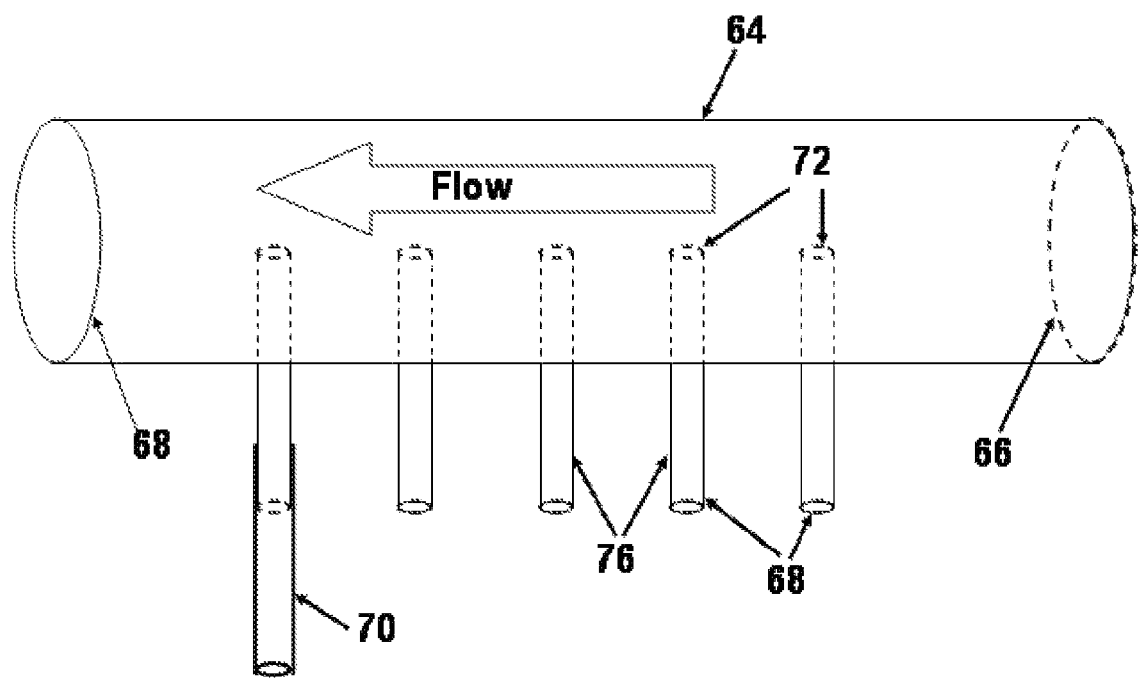
FIG. 8 illustrates a preferred manifold design.

One suitable manifold is illustrated in FIG. 8. This manifold comprises a common channel with an inlet port (manifold inlet) 66 and an outlet port (manifold outlet) 68. In fluid communication with the manifold are a number of capillary connectors 76 that each with an internal (manifold) capillary port 72, and an external capillary port 68. Each capillary connector is disposed to receive a connection (e.g. a tubing connection) to provide a fluid communication to a spotting capillary 12. The internal capillary port 72 is disposed inwards into the manifold so that the capillary port is not flush with the internal wall of the manifold. This prevents droplets from accumulating on the internal capillary port 72 which could interfere with reliable loading or delivery of samples.

The manifold can be made of any of a variety of materials and can take a number of different shapes. Preferred shapes however, permit the rapid distribution of pressure, permit the unidirectional flow of gas and waste, and permit the disposition of the internal ports 72 away from the internal surface of the manifold. Useful materials, include various plastics, glass, quartz, ceramic, and metals. In one preferred embodiment, the manifold is fabricated from stainless steel.

Figure 9:
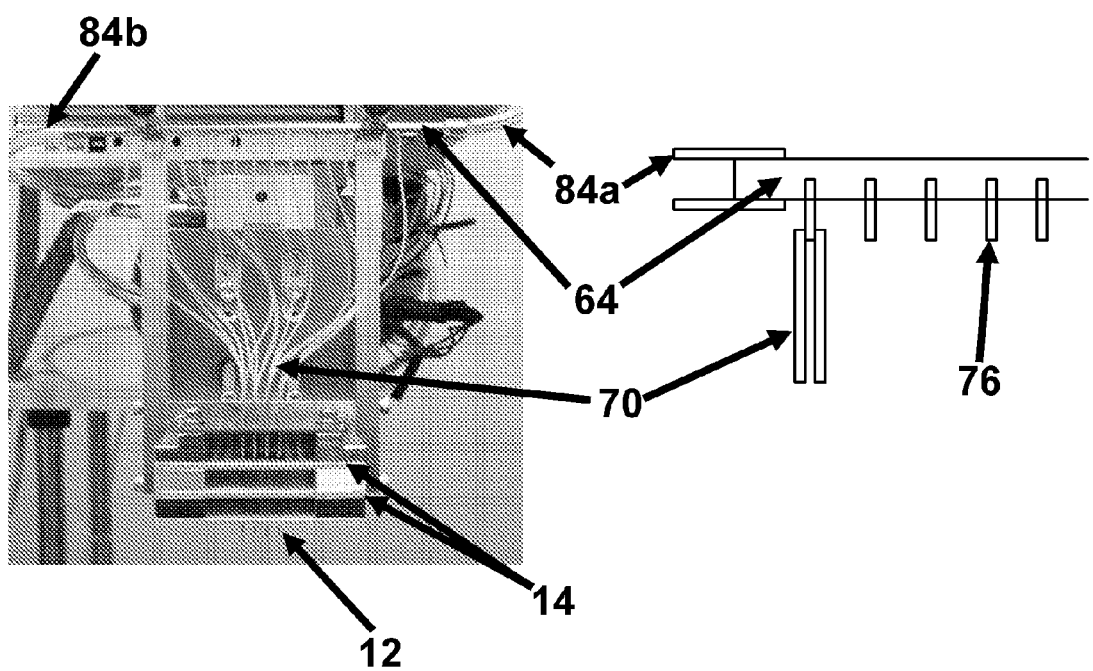
FIG. 9 illustrates the print head and its associated plumbing.

A plumbed print head is illustrated in FIG. 9. This figure illustrates the print head 10 comprising a plurality of spotting capillaries 12 (four visible in the figure). The spotting capillaries are in fluid communication with the manifold 64 via flexible capillary tubing 70. A pressure line 84a can be seen at the upper right and a waste/vacuum line 84b can be seen at the upper left.

Figure 10:
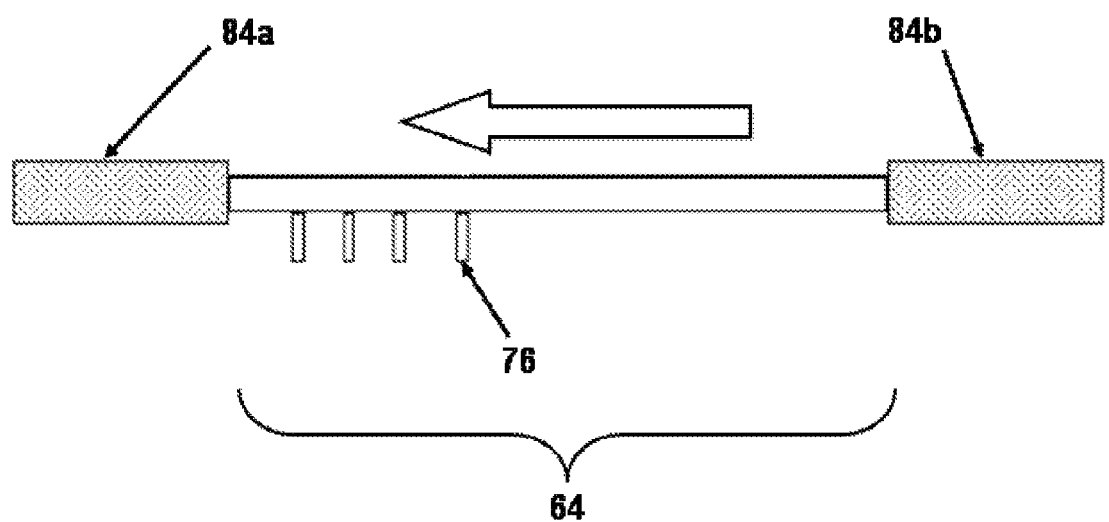
FIG. 10 illustrates unidirectional flow through a manifold according to the methods and devices of this invention. The manifold 64 is connected to flexible tubing 84a leading to a vacuum source and to flexible tubing 84b leading to a pressure source. Flow is unidirectional in the direction of the open arrow.
Figure 11:
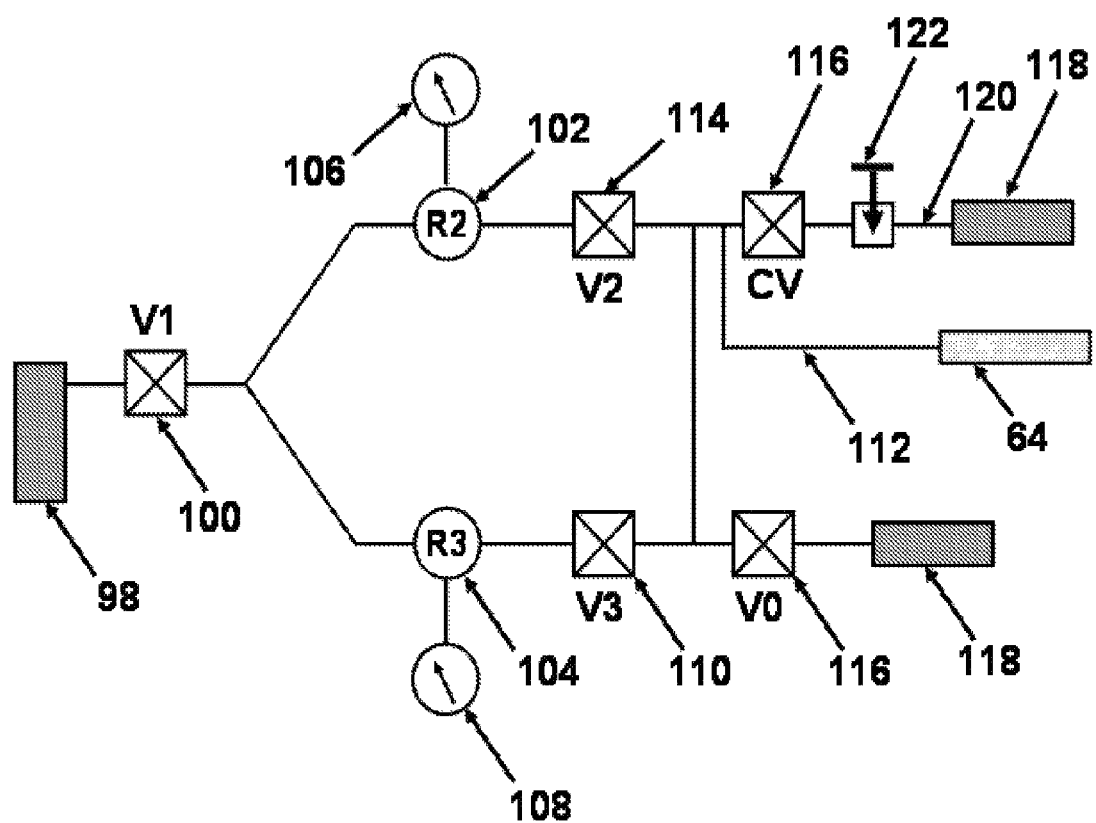
FIG. 11 schematically illustrates controls for the pressure side of the pressure control system for printhead operation.
Figure 12:
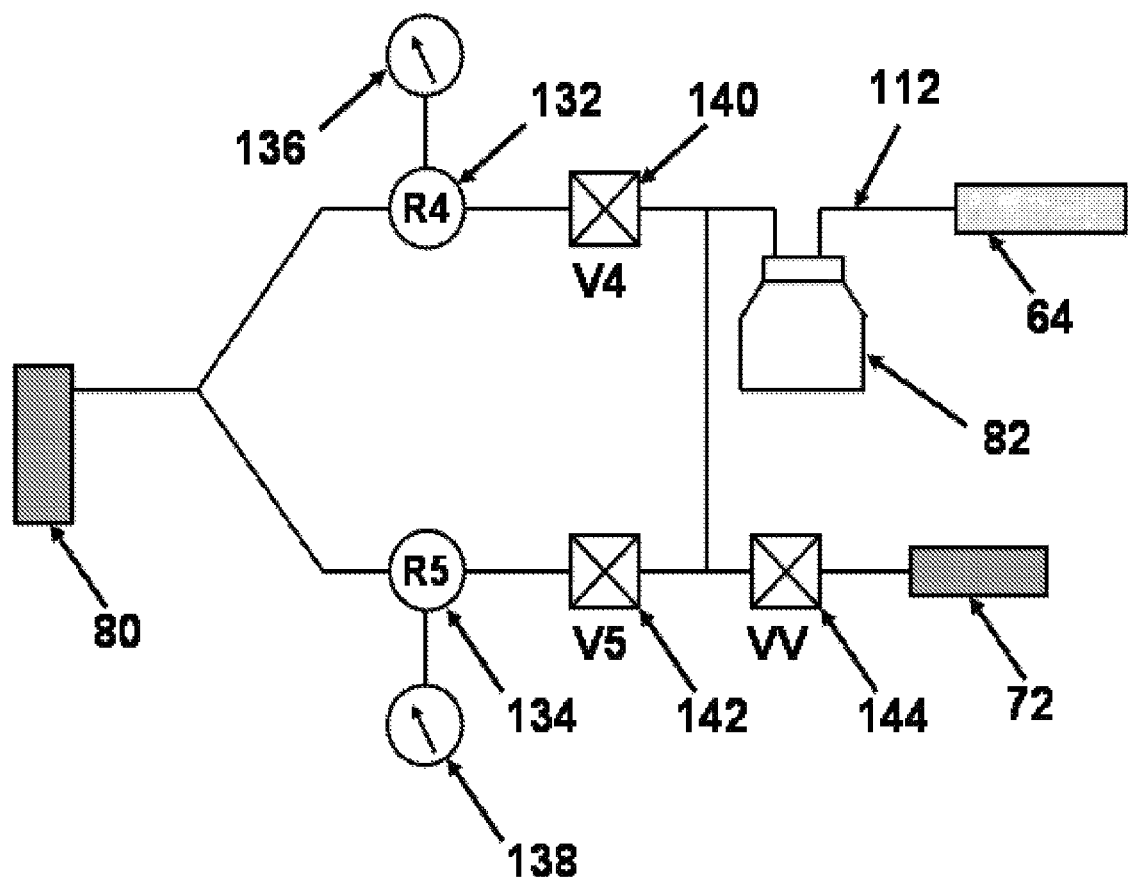
FIG. 12 schematically illustrates controls for the vacuum side of the pressure control system for printhead operation.

Another pressure/vacuum system is illustrated in FIGS. 10, 11 and 12. This pressure/vacuum system for managing the print head permits operation in a larger format printer where tubing between the print head and pressure and vacuum sources is sufficiently long so that the volume and flow impedance of the tubing has a significant impact on printer operation. The basic operating concept is to assure that flow of gas or liquid in the manifold is always towards the waste bottle as shown by the arrow in FIG. 10. This prevents liquid that may be in present the line going from the manifold to the waste bottle from flowing back into the manifold and blocking the tubes that supply pressure and vacuum to the printing pins. When large amounts of liquid are present in the manifold, for example during a wash cycle, sufficient air flow is maintained in the manifold to rapidly sweep the fluid into the waste bottle. The controls for the pressure side of the system are illustrated in FIG. 11, and those for the vacuum side are illustrated in FIG. 12.

As shown in FIG. 11, A pressure source 98 (e.g. N2 tank) is connected through a printhead supply valve V1 100 to a medium (blowout) pressure regulator R2 102 (e.g. ~20 psi) and to a very low (printing) pressure (e.g., ~0-0.5 in $H_2O$) regulator R3 104. The regulators are optionally connected to a blowout pressure readout 106, and/or to a very low pressure readout 108. The very low pressure side is connected through a very low (printing) pressure valve V3 110 to a line 112 leading to the high pressure side of the manifold 64. The medium pressure side is connected through V3 medium (blowout) pressure valve V2 114 to a line 90 leading to the high pressure side of the manifold 64. The low pressure side is also vented to a vent through vent valve V0 116 to a vent 118.

As shown in FIG. 12 vacuum source 80 is connected to a coarse vacuum regulator R4 132 maintaining a "vacuum" of about 20 in Hg, and to a medium vacuum regulator R5 134 maintaining a "vacuum" of about 15 in Hg. The two regulators can, optionally, be connected to "coarse vacuum" and medium vacuum readouts 136 and 138, respectively. The line from the coarse side vacuum regulator connects via a coarse (wash) vacuum valve V4 140 to a waste receptacle 82 which is also connected via a vacuum line 146 to the manifold 64 as shown. The line from the coarse side vacuum regulator connects via a vacuum valve V5 142 to the waste receptacle 82 and via a vacuum vent valve VV 144 to a vent 72 as illustrated.

Two features contribute to maintaining unidirectional flow and rapidly clearing liquid from the manifold. Liquid clearing is assured by the vent line 120 containing connecting to the vent 118 and containing a needle valve 122, which is controlled by the "constrictor valve" 116 in FIG. 11. This has particular use when washing the print head. At some times during the washing the tips of the printing pins are immersed in liquid and a vacuum is applied. This draws liquid into the pins and up into the manifold. Opening constrictor valve 116, allows a small amount of air to enter the pressure side of the system, and sweeps the liquid out of the manifold and to the waste bottle. The amount of flow is determined by adjusting the needle valve.

Unidirectional flow is accomplished always applying vacuum to one side of the manifold, and pressure to the other, and by providing atmospheric vents on both the pressure and vacuum sides of the system. The vents are controlled by valves V0 116 and VV 144 respectively. In combination with valve CV 116, this permits rapidly returning the system to atmospheric pressure without having a period of flow in reverse direction.

For example, during a wash cycle where vacuum is applied, all of the tubing in the system including that on the high pressure side of the manifold, is below atmospheric pressure. If the only atmospheric vent were on the vacuum side of the system, opening that vent would result in flow from the low pressure side toward the manifold as the tubing filled with air. Conversely, when the system is pressurized in order to blow out any liquid that may be in the printing pins, the tubing and waste bottle are at elevated pressure. If the only atmospheric vent were on the high pressure side of the system, then the gas in the waste bottle would flow towards the manifold when this vent was opened. Both of these reverse flows may be large enough to transport any liquid that may be in the tubing connecting the manifold to the waste bottle back towards the manifold, perhaps causing some to enter the manifold. The flow reversals can either be entirely eliminated or reduced to acceptable levels by using vents on both the pressure and vacuum sides of the system. Opening both vent valves, V0 116 and VV 144, simultaneously permits returning the system to atmospheric pressure without substantial flow reversal. The dual vents V0 and VV also provide the advantage of returning the system to atmospheric pressure rapidly since VV can be physically close to the waste bottle, reducing the flow impedance between it and the vent.

B) Representative Print Cycle.

Valve V1 100 is typically open continually during printing. A typical print operation begins by cleaning the printing pins. The tips of the pins are dipped into a sonication bath containing a dilute solution (approximately 1 part in 10,000 in distilled water) of glass cleaning solution, (Micro 90). Pressure may be applied to expel the contents of the pins by opening valve V2 114 or V3 110. Subsequently, vacuum is applied to the manifold by opening valve V4. Valve CV is also opened to provide air flow through the manifold. The vacuum draws cleaning fluid into the printing pins and up to the manifold, where the air flow sweeps it rapidly to the waste bottle. The print head is dipped into the cleaning fluid several times with the vacuum applied so that some air enters the printing pins when they are raised above the fluid. Each dip cycle last approximately 1 sec. Alternating regions of air and liquid travel up the printing pins and their associated tubing to the manifold. The interspersed regions of liquid and air provide more rapid removal of residual printing solutions from the printing pins than would be obtained if the tips of the pins were just dipped into the wash solution and remained continuously immersed.

The print head is then moved over a second sonication bath that contains distilled water and the tips of the pins are periodically immersed several times with valves V4 140 and CV 116 open. Each dip cycle last approximately 1 sec. This draws water through the pins to remove the cleaning solution. The print head is then moved to a drying station where warm air is blown over the printing pins for approximately 5-10 seconds. During this time, pressure may be applied for a period to blow liquid out of the pins by opening V2 114 and closing the other valves. The remainder of the drying time vacuum is applied by opening V4 140, and CV 116 is opened to allow airflow to dry the manifold.

After the drying period V4 and CV are closed and atmospheric vents VV 144 and V0 116 are opened to bring the system to ambient pressure. The print head is then positioned over the microtiter plate and the tips of the printing pins are immersed in printing solutions from the desired position in the plate. VV 144 and V0 116 are closed. A vacuum pulse is applied by opening V5 142 in order to begin the loading of printing solutions into the pins. After ~0.1-1.0 sec V5 is closed and the atmospheric vents VV 144 and V0 116 are opened to return the system to ambient pressure. Loading of the printing solutions continues for ~1-2 sec using capillary action. The printing pins are then lifted out of the printing solutions and VV and V0 closed.

The print head is then moved to its printing position and valve V3 110 is opened to apply a low, constant, pressure of 0.0-0.5 inches of water to the printing pins. This pressure assures that the printing solutions remain at the tips of the printing pins so that the tips remain wet with printing solution. Varying the pressure provides some control over the amount of liquid that is deposited when the printing pins contact the array substrates. The pressure is kept low enough so that the printing solutions are not ejected from the pins. The tips of the pins are contacted with the array substrates at all of the locations specified by the operator. After completion of the printing with the current load of printing solutions, the cycle starts again with the print head being moved over the first sonicator bath, the tips lowered into it, and the unused printing solutions expelled.

VI. Preparation of a Microarray.

The microarray printer of this invention can be used to print microarrays comprising essentially any molecules that can be suspended, dissolved, or otherwise placed in a solution. Preferred microarrays include, but are not limited to microarrays of biomolecules (e.g. sugars, carbohydrates, nucleic acid, proteins, and the like). Particularly preferred microarrays include nucleic acid and/or protein arrays. Methods of preparing and/or purifying biomolecules are well known to those of skill in the art (see, e.g., Berger and Kimmel (1989) *Guide to Molecular Cloning Techniques*, Methods in Enzymology 152 Academic Press, Inc., San Diego, Calif.; Sambrook et al. (1989) *Molecular Cloning—A Laboratory Manual* (2nd ed.) Vol. 1-3, Cold Spring Harbor Laboratory, Cold Spring Harbor Press, NY; Ausubel et al. (1994) *Current Protocols in Molecular Biology*, Current Protocols, a joint venture between Greene Publishing Associates, Inc. and John Wiley & Sons, Inc., (1994 Supplement) (Ausubel); U.S. Pat. No. 5,017,478; and European Patent No. 0,246,864.).

The materials that are to be printed (e.g. proteins, nucleic acids, etc.) are typically formulated in "printing solutions". Solutions for microarray printing are well known to those of skill in the art (see, e.g., U.S. Pat. Nos. 6,101,946, 5,958,342; and MacBeath and Schreiber (2000) *Science* 289: 1760-1763; Mark Schena (Ed.) (1999) *Genes, Genomes and Chips. In DNA Microarrays: A Practical Approach*, Oxford University Press, Oxford).

The microarrays can be fabricated on any of a wide variety of substrates well known to those of skill in the art. Such substrates include, but are not limited to glass, plastic, quartz and other minerals, metal, ceramic, porcelain, metal covered (e.g. sputtered) glass, and the like. A number of substrates, often derivatized to facilitate microarray printing are commercially available (see, e.g., silane slides from Sigma Chemical Co., the SuperClean™, SuperAmide™, and SuperAldehyde™ substrates from Telechem, International Inc., etc.).

In operation, the printing pins (spotting capillaries) are initially washed. In a preferred embodiment, this involves moving the print head over a wash bath and applying pressure (e.g., about 15 PSI) to the manifold to blow out any liquid remaining in the spotting capillaries. The spotting capillaries are dipped in and out of a cleaning solution (e.g. 0.001% Micro-90, Cole Palmer Inc.), in a sonicating bath at about 0.75 sec intervals for about 3 cycles while pressurized.

The device is switched from pressure to house ("high") vacuum and the spotting capillaries are dipped into the sonicated cleaning solution for 3 more cycles while drawing cleaning solution into the spotting capillaries. The spotting capillaries are then moved to a sonicating rinse bath that contains pure (e.g. double distilled) water.

The spotting capillaries are dipped in and out of water for about 3 cycles of about 0.75 sec each, with vacuum applied. This allows the formation of interspersed air bubbles and water in the tubing, assuring that the cleaning solution is more effectively removed from the walls of the tubes. Finally the spotting capillaries are dried by sucking air through them using house vacuum, blowing hot air over the spotting capillaries for about 4 sec, opening a vent to atmosphere and continuing vacuum for about 2 sec in order to clear liquid from the manifold and waste tubing (see FIG. 7).

The spotting capillaries are then filled by dipping the spotting capillaries into reagent reservoir(s) (e.g. a microtiter plate) containing the printing solution(s). Full house vacuum is applied to the manifold for about 0.15 sec in order to assure that the solutions enter the tips of the pins. The manifold is then vented to atmospheric pressure and the spotting capillaries are allowed to sit in the printing solutions for about an additional 0.75 sec so that capillary action fills the spotting capillaries. In one preferred embodiment, the spotting capillaries each contain approximately 0.2 ml when full. The spotting capillaries do not fill beyond their tops due to capillary action—the solutions do not enter the flexible tubing that connects the pins to the manifold. In some cases a slight vacuum of ~0.2 inches of water is used to assist the filling. This is adjusted to be low enough so that the no liquid is drawn beyond the top of the pins. The entire wash, dry and fill functions take about 25 seconds.

To print an array feature or features, the print head is moved over the first printing substrate and lowered to make contact, and raised. In one preferred embodiment, in the upper position the tips of the printing pins are about 0.5 to 1.0 mm above the array substrate, and when printing the print head is lowered so that the pins would move about 0.2 mm below the substrate surface if no array substrate were present. When a substrate is present the spotting capillary tips contact it and the spring mounts allow the spotting capillaries to stop moving while the print head body continues its motion toward the substrate. In a preferred embodiment, the total time for the print head to move down, contact the slide and return to the upper position is about 0.05 to 0.2 sec. During the printing operation a constant pressure of 0.1 to 0.4 inches of water is applied to the manifold to keep the printing solutions at the tips of the spotting capillaries. This assures that the spotting capillaries are wet with the printing solutions so that liquid will be transferred to the substrate on contact. The pressure does not eject the printing solution. If this is not done, the solutions can pull away from the tips and the printing will stop. The small diameter of the tubing and the printing pins provides enough flow resistance to air so that the manifold pressure is maintained even if one or more of the pins does not contain printing solution. The cycle is repeated to print additional features or other array substrates.

The amount of printing solution that is deposited on the substrate depends on the interaction between the substrate and the printing solution, and the diameter of the tip of the printing pin. When printing salt solutions on glass, each fill of the printing pin (0.2 ml) can make at least 10,000 spots. When printing 20% DMSO solutions with DNA, the same load can print at least 2000 spots. This is many more spots than are possible with other printing systems. Thus the system described above can deposit less than 100 pL per spot in typical printing.

Use of the novel spotting capillaries and/or print heads of this invention provides extremely efficient reagent usage. In certain embodiments, the printer can print at least about 500 spots (features) per 0.2 μL load, more preferably at least about 1000 spots (features) per 0.2 μL load, most preferably at least about 1500 spots (features) per 0.2 μL load, at least about 2000 spots (features) per 0.2 μL load, at least about 5,000 spots (features) per 0.2 μL load, or at lest about 10,000 spots (features) per 0.2 μL load. Because the printing capacities are so high, the print head typically does not need to refill during a print run. This greatly decreases the duration of a print run when a large number of arrays are made at one time.

VII. Microarray Printing Device.

The various elements described above, e.g. spotting capillaries, print head design, array support platen, print head support platen, vacuum and pressure system, manifold, sample loading unloading protocols, and the like can be incorporated individually, or in combination, into preexisting microarray printers or they can be assembled into a microarray printer built de novo.

Methods of designing and building microarray printing devices are generally known to those of skill in the art (see, e.g., U.S. Pat. Nos. 6,110,426, and 5,807,522, and publications of the Brown Laboratory at Stanford University (e.g., *The McGuide. Version* 2.0, available on the internet at http://cmgm.stanford.edu/pbrown/mguide/index.html, and from Cold Spring Harbor Laboratories).

In general, microarray printers of this invention will, in preferred embodiments, include a base adapted to hold reservoir(s) of printing solutions, a platen for supporting and positioning microarray substrates, and a platen for supporting and positioning a print head. The microarray printer will include actuators (e.g. motors) for driving/positioning the various platens and for vertically positioning the print head. The microarray printer, will typically include associated electronics to read encoded platen positions and/or to drive the various actuators to position the array substrates and print head. Typically such electronics will include a computer controller. The microarray printer can additionally comprise vacuum and pressure lines, reagent reservoirs, waste receptacles, cleaning baths and the like as described herein.

In a particularly preferred embodiment, the microarray printer will include the print head platen, the array substrate platen, a print head comprising spotting capillaries as described herein. The microarray printer will also preferably also include pressure and vacuum sources as described herein. While it is preferred that the microarray printer comprise all of the elements described herein, it is not required that all such elements be present. Thus, in certain embodiments, the microarray printer comprises one, two, or only a few of such elements. Thus, for example certain microarray printers may only comprise a print head according to this invention and/or the array substrate platen, and/or the print head support platen, and so forth.

VIII. Microarrays.

It is believed that the microarray printers of this invention permit the production of spotted microarrays with an accuracy, consistency, and array feature density previously unavailable. Thus, in certain embodiments, this invention provides high-density microarrays comprising a plurality of molecules, preferably biomolecules where the array comprises at least about 1,000 features (spots), preferably at least about 10,000 features (spots), more preferably at least about 40,000 features (spots), and most preferably at least about 100,000 features (spots), or at least about 1,000,000 features (spots). In particularly preferred embodiments, the features are present at an average center-to-center spacing of about 130 μm or less, preferably about 100 μm or less, more preferably about 80 μm or less, and most preferably about 65, 50, or 40 μm or less.

In certain embodiments, the microarray is a protein and/or nucleic acid microarray. In nucleic acid arrays unlike chemically synthesized arrays, the printed arrays of this invention are not limited by the size of nucleic acid. Large nucleic acids can be printed as easily as small nucleic acids (e.g. oligonucleotides less than 20-30 mer). Indeed, there is no size limit on the printed nucleic acids and the particular nucleic acid sizes depends on the intended use of the array. Arrays printed according to the methods of this invention typically have a fragment size ranging from about 100 to about 1000 bases (e.g. a mixture of PCR fragments). Thus, frequently nucleic 100 nucleotides or longer are printed. Fragment sizes ranging from about 1000 bases to about 10,000 bases or from about 10,000 bases to about 100,000 bases or larger can be readily accommodated.

Preferred arrays of this invention have a feature (spot) density greater than about 5,000, 10,000, or 20,000 features/$cm^2$, preferably greater than about 30,000 features/$cm^2$, more preferably greater than about 40,000 features/$cm^2$, and most preferably greater than about greater than about 50,000 or 60,000 features/$cm^2$.

Because the reagents are typically simply spotted, in preferred embodiments, the molecule(s) comprising the array features are simply adsorbed to said substrate. However, in certain embodiments the reagents and/or the array substrate can be derivatized so that the molecules comprising the features (spots) covalently couple to the substrate. Methods of so derivatizing macromolecules are well known to those of skill in the art. Thus, for example, the reagents can be derivatized with a sulfhydryl group (—SH) which will covalently couple to a gold surface (e.g. gold coated glass).

IX. Kits.

In still another embodiment, this invention provides kits comprising one or more containers containing the arrays described above. In certain embodiments, the arrays will comprise features representing nucleic acids from every chromosome in a subject organism (e.g. a human). In certain embodiments, the arrays will comprise features representing nucleic acids from every known expressed sequence tag (EST) for a given organism, or tissue, or whose expression is associated with a particular physiological state (e.g., a particular pathology).

These array constituents are merely illustrative. Numerous other arrays components will be recognized by one of ordinary skill in the art.

In certain embodiment, the kits can, optionally, additionally contain one or more of the following: detectable labels, hybridization reagents, software, buffers, and the like.

It is understood that the examples and embodiments described herein are for illustrative purposes only and that various modifications or changes in light thereof will be suggested to persons skilled in the art and are to be included within the purview of this application and the scope of the appended claims. All publications, patents, and patent applications cited herein are hereby incorporated by reference in their entirety for all purposes.

What is claimed is:

1. A method of printing a microarray, said method comprising:
   providing an array substrate in a microarray printing device, said printing device comprising:
   a microarray substrate holder attached to a platen wherein said substrate holder contains said array substrate; and
   a microarray print head, said print head comprising:
   a plurality of spotting capillaries disposed in a support that permits the spotting capillaries to move in a direction parallel to the long axis of said capillaries, wherein said capillaries are coupled to pistons;
   a vacuum chamber comprising an upper wall and a lower wall through which the capillaries and the pistons are disposed; and
   a port in said chamber to which a vacuum can be applied;
   wherein said pistons and capillaries are disposed such that increasing the vacuum in said chamber increases a force holding the pistons into the chamber and thereby increases the resistance of said capillaries to deflection away from a printing substrate;
   providing a series of solutions comprising reagents that will form features of said microarray; and
   operating said microarray printing device to print said micro array on the array substrate.

2. The method of claim 1, wherein said microarray printing device prints a microarray comprising at least 1,000 different array elements.

3. The method of claim 1, wherein said microarray printing device prints a microarray comprising having an average inter-feature spacing of no more than about 130 μm.

4. The method of claim 1, wherein said microarray is a nucleic acid microarray.

5. The method of claim 1, wherein said microarray is a protein microarray.

6. The method of claim 1, wherein said microarray is a small an organic molecule microarray.

7. The method of claim 1, wherein said substrate is a glass substrate.

8. The method of claim 1, wherein said substrate is a metal-coated glass substrate.

9. The method of claim 1, wherein said microarray printing device comprises a manifold in fluid communication with said capillaries.

10. The method of claim 9, wherein said microarray printing device applies vacuum to said manifold to load a spotting capillary.

11. The method of claim 9, wherein the vacuum is applied as one or more pulses.

12. The method of claim 9, wherein said microarray printing device applies positive pressure to the manifold when dispensing from a spotting capillary to the substrate.

13. The method of claim 1, wherein said method comprises loading feature-forming reagents from a microtiter plate comprising at least about 864 wells.

14. The method of claim 11, wherein the duration of each of said one or more pulses is less than about 0.5 sec.

15. The method of claim 1, wherein each capillary is coupled to a single piston.

16. The method of claim 1, wherein one or more capillaries are coupled to a single piston.

17. The method of claim 1, wherein said print head further comprises a means for adjusting the vacuum in said chamber.

18. The method of claim 1, wherein the lower wall of said chamber comprises a plurality of tapered guide holes in which said capillaries are disposed.

19. The method of claim 1, wherein the lower wall of said chamber comprises two or more guide plates such that lateral movement of said capillaries is constrained at two or more positions.

20. The method of claim 1, wherein the lower wall of said chamber comprises two guide plates such that lateral movement of said capillaries is constrained at two positions.

21. The method of claim 1, wherein said spotting capillaries pass through an upper end of the pistons.

22. The method of claim 1, wherein said spotting capillaries are attached to an upper portion of the pistons at an upper portion of the capillaries.

23. The method of claim 1, wherein said capillaries are spaced to accommodate a standard 864 well microtiter plate.

24. The method of claim 1, wherein said capillaries are spaced to accommodate a standard 1536 well microtiter plate.

25. The method of claim 1, wherein the distance between adjacent spotting capillaries is about 3 mm or less, center to center.

26. The method of claim 1, wherein said spotting capillaries are glass or quartz.

27. The method of claim 1, wherein said spotting capillaries have a beveled tip.

28. The method of claim 27, wherein said beveled tip is ground.

29. The method of claim 1, wherein a capillary in said print head has maximum load volume of about 0.5 μL.

30. The method of claim 1, wherein a capillary in said print head has a minimum load volume of about 0.05 μL.

31. The method of claim 1, wherein a capillary in said print head has a load volume of about 0.2 μL.

32. The method of claim 1, wherein said print head comprises at least 4 spotting capillaries.

33. The method of claim 1, wherein said print head comprises at least 16 spotting capillaries.

34. The method of claim 1, wherein said print head comprises from 16 to about 256 capillaries.

35. The method of claim 1, wherein said capillaries are in fluid communication with a manifold.

36. The method of claim 35, wherein said manifold comprises at least one common port and individual ports wherein an aperture into an individual port is disposed inward of the inside wall of said manifold.

37. The method of claim 1, wherein said printing device prints at least 5,000 array elements per spotting capillary per load.

38. The method of claim 1, wherein said printing device prints array elements with a precision of at least 30 μm.

39. The method of claim 1, wherein said printing device prints array elements with an average inter-element spacing 130 μm or less.

40. The method of claim 9, wherein said microarray printer utilizes pressure and vacuum to control reagent loading or dispensing.

41. The method of claim 1, wherein said device prints more than 200 microarray substrates in a run.

42. The method of claim 1, wherein said device loads reagents from a microtiter plate comprising at least about 864 wells.

43. The method of claim 1, wherein said device loads reagents from a microtiter plate comprising at least about 1536 wells.

44. The method of claim 1, wherein said device comprises means for applying positive or negative pressure to the spotting capillaries and/or to the chamber in the print head.

* * * * *